(12) United States Patent
Li et al.

(10) Patent No.: US 11,713,348 B2
(45) Date of Patent: Aug. 1, 2023

(54) SCFV AMINO ACID SEQUENCE, CHIMERIC ANTIGEN RECEPTOR CONTAINING SAME AND APPLICATION THEREOF

(71) Applicant: GUANGDONG ZHAOTAI INVIVO BIOMEDICINE CO.,LTD, Guangdong (CN)

(72) Inventors: Peng Li, Guangdong (CN); Ruocong Zhao, Guangdong (CN); Zhaoyang Tang, Guangdong (CN); Le Qin, Guangdong (CN); Yuanbin Cui, Guangdong (CN); Simiao Lin, Guangdong (CN); Yao Yao, Guangdong (CN)

(73) Assignee: GUANGDONG ZHAOTAI INVIVO BIOMEDICINE CO., LTD, Guangdong (CN)

(*) Notice: Subject to any disclaimer, the term of this patent is extended or adjusted under 35 U.S.C. 154(b) by 389 days.

(21) Appl. No.: 16/957,647

(22) PCT Filed: Mar. 8, 2019

(86) PCT No.: PCT/CN2019/077492
§ 371 (c)(1),
(2) Date: Jun. 24, 2020

(87) PCT Pub. No.: WO2020/155310
PCT Pub. Date: Aug. 6, 2020

(65) Prior Publication Data
US 2021/0238253 A1    Aug. 5, 2021

(30) Foreign Application Priority Data
Jan. 28, 2019 (CN) .......................... 201910081590.8

(51) Int. Cl.
*C07K 14/705* (2006.01)
*A61P 35/00* (2006.01)
(Continued)

(52) U.S. Cl.
CPC ........ *C07K 14/70521* (2013.01); *A61K 45/06* (2013.01); *A61P 35/00* (2018.01); *C07K 16/2803* (2013.01); *A61K 38/00* (2013.01)

(58) Field of Classification Search
CPC .......... C07K 14/70521; C07K 16/2803; A61K 45/06; A61K 38/00; A61P 35/00
See application file for complete search history.

(56) References Cited

U.S. PATENT DOCUMENTS

| 2011/0065902 A1* | 3/2011 | Sleeman | ........ C12Y 304/21061 530/389.1 |
| 2018/0153977 A1* | 6/2018 | Wu | .......................... A61P 35/00 |

FOREIGN PATENT DOCUMENTS

| CN | 106220736 | 12/2016 |
| CN | 107207613 | 9/2017 |

(Continued)

OTHER PUBLICATIONS

Chailyan, A., et al. (2011) The association of heavy and light chain variable domains in antibodies: implications for antigen specificity FEBS Journal 278; 2858-2866 (Year: 2011).*

(Continued)

*Primary Examiner* — Scarlett Y Goon
*Assistant Examiner* — Audrey L Buttice
(74) *Attorney, Agent, or Firm* — Workman Nydegger

(57) ABSTRACT

The present disclosure relates to a scFv amino acid sequence capable of recognizing CD19 antigen and a nucleotide sequence encoding the same, and also relates to a chimeric antigen receptor, a nucleic acid encoding the same and a cell expressing the same, and their uses in the manufacture of a (Continued)

medicament for treating tumors. The chimeric antigen receptor of the present disclosure comprises at least one extracellular domain, an optional transmembrane domain and at least one intracellular costimulatory signaling domain, wherein the extracellular domain comprises a CD19 antigen-recognizing and binding domain. The chimeric antigen receptor of the present disclosure has been humanized, resulting in a longer survival period in vivo, and a corresponding extended complete remission period in patients.

14 Claims, 10 Drawing Sheets

Specification includes a Sequence Listing.

(51) Int. Cl.
*A61K 45/06* (2006.01)
*C07K 16/28* (2006.01)
*A61K 38/00* (2006.01)

(56) References Cited

FOREIGN PATENT DOCUMENTS

| | | |
|---|---|---|
| CN | 107226867 | 10/2017 |
| CN | 107312091 | 11/2017 |
| CN | 107383196 | 11/2017 |
| CN | 108070607 | 5/2018 |
| CN | 108383914 | 8/2018 |
| CN | 110248677 | 9/2019 |
| JP | 2016-514462 A | 5/2016 |
| JP | 2017522862 | 8/2017 |
| JP | 2017526370 | 9/2017 |
| JP | 2018527021 | 9/2018 |
| JP | 2018537520 | 12/2018 |
| WO | WO2013169691 | 11/2013 |
| WO | WO-2016081748 A2 * | 5/2016 ........... A61K 39/395 |
| WO | WO2017184619 A2 | 10/2017 |
| WO | WO2017184619 A3 | 10/2017 |
| WO | 2018/200496 A1 | 11/2018 |

OTHER PUBLICATIONS

Rabia, L., et al (2018) Understanding and overcoming trade-offs between antibody affinity, specificity, stability, and solubility Biochem Eng. J. 15(137); 365-374 (Year: 2018).*

European Search Report received for EP Patent Application No. 19897536.9, dated Jul. 28, 2021, 11 pages.

Weng, Jianyu, et al., "A novel generation 1928zT2 CART cells induce remission in extramedullary relapse of acute lymphoblastic leukemia", Journal of Hematology & Oncology, vol. 11. Issue 1, 2018, pp. 1-12.

European Search Report issued in Application No. / Patent No. 19897536.9-1111 / 3715373 PCT/CN2019077492 dated Jul. 28, 2021.

Weng, Jianyu, et al., "A novel generation 1928zT2 CAR T cells induce remission in extramedullary relapse of acute lymphoblastic leukemia", Journal of Hematology & Oncology (2018).

Lai, et al., "Toll-like receptor 2 costimulation potentiates the anti-tumor efficacy of CAR T Cells", Leukemia (2017).

Japanese Office Action cited in Application No. 2020-513619 dated May 12, 2021.

International Search Report issued in PCT/CN2019/077492 dated Sept. 9, 2019, Issue date on document is Sep. 16, 2019.

Ni Fang, et al., "Application Progress of Chimeric Antigen Receptor T Cells in B Cell Lymphoma", Chinese Journal of Cell Biology 2018, 40(13): 2260-2268.

Bipulendu Jena, et al., "Chimeric Antigen Receptor (CAR)—Specific Monoclonal Antibody to Detect DC19-Specific T Cells in Clinical Trials" Plos ONE, Mar. 2013, vol. 8, Issue 3.

Chinese Office Action cited in Application No. 201910081590.8 dated Dec. 14, 2021.

Japanese Office Action cited in Application No. 2020-513619 dated Nov. 1, 2021.

* cited by examiner

SEQUENCE LISTING

```
<160> NUMBER OF SEQ ID NOS: 12

<210> SEQ ID NO 1
<211> LENGTH: 133
<212> TYPE: PRT
<213> ORGANISM: Artificial sequence
<220> FEATURE:
<223> OTHER INFORMATION: amino acid sequence of a heavy chain

<400> SEQUENCE: 1

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Arg His
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Gln Tyr Tyr Val Asp Ser Val
    50                  55                  60

Lys Gly Arg Phe Thr Ile Ser Arg Asp Asn Ser Lys Asn Thr Leu Asp
65                  70                  75                  80

Leu Gln Met Asn Ser Leu Arg Val Glu Asp Thr Ala Val Tyr Tyr Cys
                85                  90                  95

Ala Arg Arg Ser Ile Thr Trp Tyr Gly Gly Phe Asp Ile Trp Gly Gln
            100                 105                 110

Gly Thr Met Val Thr Val Ser Ser Ala Gln Thr Thr Ala Pro Ser Val
        115                 120                 125

Tyr Pro Leu Ala Pro
    130

<210> SEQ ID NO 2
<211> LENGTH: 133
<212> TYPE: PRT
<213> ORGANISM: Artificial sequence
<220> FEATURE:
<223> OTHER INFORMATION: amino acid sequence of a heavy chain

<400> SEQUENCE: 2
```

```
Gln Val Gln Leu Val Glu Ser Gly Gly Gly Val Val Gln Pro Gly Arg
1               5                   10                  15

Ser Leu Arg Leu Ser Cys Glu Ala Ser Gly Phe Thr Phe Ser Arg His
            20                  25                  30

Gly Met His Trp Val Arg Gln Ala Pro Gly Lys Gly Leu Glu Trp Val
        35                  40                  45

Ala Val Ile Phe Tyr Asp Gly Ser Gln Asn Tyr Tyr Ala Asp Ser Val
    50                  55                  60

Arg Gly Arg Phe Thr Ile Ser Arg Asp Asn Ser Lys Asn Thr Leu Ser
65                  70                  75                  80

Leu Gln Met Asp Ser Leu Arg Ala Glu Asp Thr Ala Val Tyr Tyr Cys
                85                  90                  95

Ala Arg Arg Ser Ile Thr Trp Asn Gly Gly Phe Asp Ile Trp Gly Gln
            100                 105                 110

Gly Thr Met Val Thr Val Ser Pro Ala Gln Thr Thr Ala Pro Ser Val
        115                 120                 125

Tyr Pro Leu Ala Pro
        130
```

```
<210> SEQ ID NO 3
<211> LENGTH: 133
<212> TYPE: PRT
<213> ORGANISM: Artificial sequence
<220> FEATURE:
<223> OTHER INFORMATION: amino acid sequence of a heavy chain

<400> SEQUENCE: 3

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Arg His
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Val Asp Ser Val
    50                  55                  60

Lys Gly Arg Phe Thr Ile Ser Arg Asp Asn Ser Lys Asn Thr Leu Asp
65                  70                  75                  80

Leu Gln Met Asn Ser Leu Arg Ala Glu Asp Thr Ala Val Tyr Tyr Cys
                85                  90                  95

Ala Arg Arg Ser Ile Thr Trp Asp Gly Ala Phe Asp Ile Trp Gly Gln
            100                 105                 110

Gly Thr Met Val Thr Val Ser Ser Ala Gln Thr Thr Ala Pro Ser Val
        115                 120                 125

Tyr Pro Leu Ala Pro
        130
```

```
<210> SEQ ID NO 4
<211> LENGTH: 133
<212> TYPE: PRT
<213> ORGANISM: Artificial sequence
<220> FEATURE:
<223> OTHER INFORMATION: amino acid sequence of a heavy chain

<400> SEQUENCE: 4

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Arg His
```

20                  25                  30
Gly Met His Trp Val Arg Gln Ala Pro Gly Lys Gly Leu Glu Trp Val
            35                  40                  45

Ala Val Ile Tyr Tyr Asp Gly Ser Asn Lys Tyr Tyr Val Asp Ser Val
        50                  55                  60

Lys Gly Arg Phe Thr Ile Ser Arg Asp Asn Ser Lys Asn Thr Leu Asp
65                  70                  75                  80

Leu Gln Met Asn Ser Leu Arg Ala Glu Asp Thr Ala Val Tyr Tyr Cys
                85                  90                  95

Ala Arg Arg Ser Ile Thr Trp Asn Gly Ala Phe Asp Ile Trp Gly Gln
            100                 105                 110

Gly Thr Met Val Thr Val Ser Ser Ala Gln Thr Thr Ala Pro Ser Val
                115                 120                 125

Tyr Pro Leu Ala Pro
            130

<210> SEQ ID NO 5
<211> LENGTH: 133
<212> TYPE: PRT
<213> ORGANISM: Artificial sequence
<220> FEATURE:
<223> OTHER INFORMATION: amino acid sequence of a heavy chain

<400> SEQUENCE: 5

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Arg His
            20                  25                  30

Gly Met His Trp Val Arg Gln Ala Pro Gly Lys Gly Leu Glu Trp Val
            35                  40                  45

Ala Val Ile Trp Tyr Asp Gly Ser Asn Lys Tyr Tyr Val Asp Ser Val
        50                  55                  60

Lys Gly Arg Phe Thr Ile Ser Arg Asp Asn Ser Lys Asn Thr Leu Asp
65                  70                  75                  80

Leu Gln Met Asn Ser Leu Arg Ala Glu Asp Thr Ala Val Tyr Tyr Cys
                85                  90                  95

Ala Arg Arg Ser Ile Thr Trp Asp Gly Ala Phe Asp Ile Trp Gly Gln
            100                 105                 110

Gly Thr Met Val Thr Val Ser Ser Ala Gln Thr Thr Ala Pro Ser Val
                115                 120                 125

Tyr Pro Leu Ala Pro
            130

<210> SEQ ID NO 6
<211> LENGTH: 138
<212> TYPE: PRT
<213> ORGANISM: Artificial sequence
<220> FEATURE:
<223> OTHER INFORMATION: amino acid sequence of a heavy chain

<400> SEQUENCE: 6

Gln Val Gln Leu Val Glu Ser Gly Gly Gly Val Val Gln Ala Gly Arg
1               5                   10                  15

Ser Leu Arg Leu Ser Cys Ala Ala Ser Gly Phe Thr Phe Ser Asn Tyr
            20                  25                  30

Gly Ile His Trp Val Arg Gln Ala Pro Gly Lys Gly Leu Glu Trp Val
            35                  40                  45

Gly Val Ile Trp His Asp Gly Ser Ile Lys Asn Tyr Ala Asp Phe Val
 50                  55                  60

Lys Gly Arg Phe Thr Ile Ser Arg Asp Asn Ser Glu Asp Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Gln Gly Asn Tyr Tyr Gly Trp Gly Ser Tyr Lys Ala Phe
            100                 105                 110

Asp Ile Trp Gly Gln Gly Thr Met Val Thr Val Ser Ser Ala Gln Thr
        115                 120                 125

Thr Ala Pro Ser Val Tyr Pro Leu Ala Pro
130                 135

<210> SEQ ID NO 7
<211> LENGTH: 106
<212> TYPE: PRT
<213> ORGANISM: Artificial sequence
<220> FEATURE:
<223> OTHER INFORMATION: amino acid sequence of a light chain

<400> SEQUENCE: 7

Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Ser Ser Trp
             20                  25                  30

Leu Ala Trp Tyr Gln Gln Lys Pro Gly Lys Ala Pro Lys Leu Leu Ile
         35                  40                  45

Tyr Lys Ala Ser Ser Leu Glu Ser Gly Val Pro Pro Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Asn Ser Ala Tyr Thr
                 85                  90                  95

Phe Gly Gln Gly Thr Lys Leu Glu Ile Lys
            100                 105

<210> SEQ ID NO 8
<211> LENGTH: 106
<212> TYPE: PRT
<213> ORGANISM: Artificial sequence
<220> FEATURE:
<223> OTHER INFORMATION: amino acid sequence of a light chain

<400> SEQUENCE: 8

Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Ser Ser Trp
             20                  25                  30

Leu Ala Trp Tyr Gln Gln Lys Pro Gly Lys Ala Pro Lys Leu Leu Ile
         35                  40                  45

Tyr Lys Ala Ser Ser Leu Glu Ser Gly Val Pro Ser Arg Phe Ser Gly
 50                  55                  60

Ser Gly Ser Gly Thr Glu Phe Thr Leu Ala Ile Ser Ser Leu Gln Pro
 65                  70                  75                  80

Asp Asp Phe Ala Thr Tyr Tyr Cys Gln Gln Tyr Asn Arg Phe Tyr Thr
                 85                  90                  95

Phe Gly Gln Gly Thr Lys Leu Glu Ile Lys
            100                 105

```
<210> SEQ ID NO 9
<211> LENGTH: 106
<212> TYPE: PRT
<213> ORGANISM: Artificial sequence
<220> FEATURE:
<223> OTHER INFORMATION: amino acid sequence of a light chain

<400> SEQUENCE: 9

Asp Ile Gln Met Thr Gln Ser Pro Ser Thr Leu Ser Ala Ser Val Gly
1               5                   10                  15

Asp Arg Val Thr Ile Ser Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Ala Tyr Thr
                85                  90                  95

Phe Gly Gln Gly Thr Lys Leu Glu Ile Lys
            100                 105

<210> SEQ ID NO 10
<211> LENGTH: 106
<212> TYPE: PRT
<213> ORGANISM: Artificial sequence
<220> FEATURE:
<223> OTHER INFORMATION: amino acid sequence of a light chain

<400> SEQUENCE: 10

Asp Ile Gln Met Thr Gln Ser Pro Ser Thr Leu Ser Ala Ser Val Gly
1               5                   10                  15

Asp Arg Val Thr Ile Ser Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Ala Tyr Thr
                85                  90                  95

Phe Gly Gln Gly Thr Lys Leu Glu Ile Lys
            100                 105

<210> SEQ ID NO 11
<211> LENGTH: 106
<212> TYPE: PRT
<213> ORGANISM: Artificial sequence
<220> FEATURE:
<223> OTHER INFORMATION: amino acid sequence of a light chain

<400> SEQUENCE: 11

Asp Ile Gln Met Thr Gln Ser Pro Ser Thr Leu Ser Ala Ser Val Gly
1               5                   10                  15

Asp Arg Val Thr Val Thr Cys Arg Ala Ser Gln Ser Ile Arg Ser Trp
            20                  25                  30
```

```
Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Asn Ser Ala Tyr Thr
                 85                  90                  95

Phe Gly Gln Gly Thr Lys Leu Glu Ile Lys
                100                 105

<210> SEQ ID NO 12
<211> LENGTH: 107
<212> TYPE: PRT
<213> ORGANISM: Artificial sequence
<220> FEATURE:
<223> OTHER INFORMATION: amino acid sequence of a light chain

<400> SEQUENCE: 12

Asp Ile Gln Leu Thr Gln Ser Pro Ser Phe Leu Ser Val Phe Val Gly
 1               5                  10                  15

Asp Arg Val Thr Ile Thr Cys Arg Ala Ser Gln Gly Ile Ser Asn Tyr
                 20                  25                  30

Leu Ala Trp Tyr Gln Gln Lys Pro Gly Lys Ala Pro Glu Leu Leu Leu
        35                  40                  45

Tyr Ala Thr Ser Thr Leu Gln Ser Gly Val Pro Ser Arg Leu Ser Gly
 50                  55                  60

Ser Gly Ser Gly Thr Glu Phe Thr Leu Thr Leu Ser Ser Leu Gln Pro
 65                  70                  75                  80

Glu Asp Phe Ala Thr Tyr Tyr Cys Gln Gln Val Tyr Ser Phe Pro Tyr
                 85                  90                  95

Thr Phe Gly Gln Gly Thr Lys Leu Glu Ile Lys
                100                 105
```

SCFV AMINO ACID SEQUENCE, CHIMERIC ANTIGEN RECEPTOR CONTAINING SAME AND APPLICATION THEREOF

SEQUENCE LISTING

The instant application contains a Sequence Listing that has been submitted electronically in ASCII format and is hereby incorporated by reference in its entirety. Said ASCII copy, created on Mar. 3, 2023, is named "20099-47_2023-03-02_Sequence-Listing_ST25" and is 13.8 kb in size.

TECHNICAL FIELD

The present disclosure relates to the technical field of cellular immunotherapy of tumors, and in particular to a scFv amino acid sequence and a nucleotide sequence encoding the same, and also relates to a chimeric antigen receptor, a nucleic acid encoding the same and a cell expressing the same, and their uses in the manufacture of a medicament for treating tumors.

BACKGROUND

Chimeric antigen receptor (CAR) T cells are those T cells on whose surface chimeric receptors which can recognize specific antigens and can transmit signals are expressed. CAR T cells play an important role in treating tumors by expressing chimeric antigen receptor (CAR) molecules which typically include an extracellular segment, a transmembrane region and an intracellular segment: the extracellular segment is a single-chain variable fragment (ScFv) formed by connecting heavy chain and light chain variable regions of an antibody via a peptide fragment; the intracellular segment is intracellular chimeras consisting of a variety of signaling molecules, including CD3zeta, CD28, OX-40, 4-1BB etc.; and the transmembrane region is originated from the transmembrane region of other molecules (such as CD8, CD4, CD28 and CD3zeta). The single chain variable fragment gene is isolated from, for example, hybridomas capable of generating monoclonal antibody which recognizes a target antigen. T cells expressing CAR molecules directly recognize antigens on the surface of tumor cells independent of the expression of major histocompatibility antigen type I on tumor cells, and at the same time activate T cells. Therefore, the T cells expressing CARs can kill tumor cells effectively. Briefly, CAR T cells recognize specific molecules on the surface of tumor cells through antigen-antibody recognition manner, and then experience activation and proliferation and exert cytotoxic function through their intracellular signaling.

For applications of humanized CD19 antibodies for the treatment of B-cell diseases such as lymphoma, leukemia, or autoimmune disease, see U.S. Patent Publication No. US2005/0070693 by Hansen. Despite recent advances in cancer therapy, B cell malignancies such as non-Hodgkin's lymphomas B cell subtypes and chronic lymphocytic leukemia are major contributors of cancer-related deaths. Accordingly, further improved therapeutic regimens for the treatment of B cell malignancies are greatly needed.

CAR-T is known as chimeric antigen receptor T cell immunotherapy, which is a novel and very popular therapeutic manner for tumor at present, and it is also considered as one of the most likely technologies to overcome malignant tumors. However, the broad application of CAR-T therapy also faces a series of challenges and bottlenecks, in that the host immune system, including T cells and antibody-mediated immunological rejection against CAR molecules, may be the key obstacles that limit the sustainability and long-term efficacy of CAR-T cells in vivo and may be one of the important factors affecting its application.

SUMMARY

The tumor-recognizing sequences currently employed in most of the registered clinical trials of CD19 CAR-T cell therapies worldwide are derived from murine-derived antibodies. After being infused into the human body, such CAR-T cells are easily recognized by the auto-immune system as xenoantigens, and thus are cleared by host T cells or antibodies, which in turn affects the sustainability of CAR T cells in vivo, resulting in a high recurrence rate and reduced long-term clinical efficacy. In view of this, the object of the present disclosure is to provide a chimeric antigen receptor and its application, specifically including a chimeric antigen receptor and a nucleic acid encoding the same, a cell expressing the same, and their application in the manufacture of a medicament for treating tumors. The CD19 antibody recognition sequence of the chimeric antigen receptor of the present disclosure has been humanized, resulting in a longer survival period in vivo, and a corresponding extended complete remission period in patients.

To achieve the above purpose, the present disclosure uses the following technical solutions:

In a first aspect, the present disclosure provides a scFv amino acid sequence capable of recognizing CD19 antigen, comprising:

a heavy chain variable region having a sequence set forth in one of SEQ ID NOs: 1-6, or a variant having at least 85% sequence identity therewith; and a light chain variable region having a sequence set forth in one of SEQ ID NOs: 7-12, or a variant having at least 85% sequence identity therewith.

In some embodiments of the present disclosure, the amino acid sequence of the heavy chain variable region of the scFv sequence has at least 85%, at least 90%, or at least 95%, such as 85%, 86%, 88%, 90%, 92%, 95%, 98%, 99% identity with an amino acid sequence set forth in one of SEQ ID NOs: 1-6; and the amino acid sequence of the light chain variable region of the scFv sequence has at least 85%, at least 90%, or at least 95%, such as 85%, 86%, 88%, 90%, 92%, 95%, 98%, 99% identity with an amino acid sequence set forth in one of SEQ ID NOs: 7-12.

In a second aspect, the present disclosure provides a nucleotide sequence encoding the scFv amino acid sequence as described in the first aspect.

In a third aspect, the present disclosure provides a chimeric antigen receptor comprising at least one extracellular domain, an optional transmembrane domain and at least one intracellular costimulatory signaling domain, wherein the extracellular domain comprises a CD19 antigen-recognizing and binding domain;

wherein the CD19 antigen-recognizing and binding domain comprises a heavy chain variable region having a sequence set forth in one of SEQ ID NOs: 1-6 or a variant having at least 85% sequence identity therewith; and the CD19 antigen-recognizing and binding domain comprises a light chain variable region having a sequence set forth in one of SEQ ID NOs: 7-12 or a variant having at least 85% sequence identity therewith.

In present disclosure, constructing humanized CD19 CAR T cells with humanized CD19-specific single-chain antibody sequences can achieve the same therapeutic effect as murine-derived CD19 CAR T cells while avoiding the immunological rejection resulted from murine single-chain antibodies. The CD19 antigen-recognizing and binding domain of the present disclosure has been humanized, which may reduce the occurrence of xenoimmune rejection without affecting the ability to recognize target antigens on tumor cells, thereby resulting in an improved duration of CAR-T cells in the human body, an enhanced immune ability to monitor tumor cells, a reduced tumor recurrence rate, and a corresponding extended complete remission period in patients.

In some embodiments of the present disclosure, the amino acid sequence of the heavy chain variable region of the CD19 antigen-recognizing and binding domain comprises a variant having at least 85%, such as 85%, 86%, 88%, 90%, 92%, 95%, 98%, 99% identity with an amino acid sequence set forth in one of SEQ ID NOs: 1-6, and having the ability to bind CD19 and induce T cell signaling, preferably a variant having at least 90%, preferably at least 95% sequence identity, and having the ability to bind CD19 and induce T cell signaling.

In some embodiments of the present disclosure, the amino acid sequence of the light chain variable region of the CD19 antigen-recognizing and binding domain comprises a variant having at least 85%, such as 85%, 86%, 88%, 90%, 92%, 95%, 98%, 99% identity with an amino acid sequence set forth in one of SEQ ID NOs: 7-12, and having the ability to bind CD19 and induce T cell signaling, preferably a variant having at least 90%, preferably at least 95% sequence identity, and having the ability to bind CD19 and induce T cell signaling.

According to the present disclosure, the CD19 antigen-recognizing and binding domain comprises a heavy chain variable region having a sequence set forth in one of SEQ ID NOs: 1-6, or a variant having at least 85%, preferably at least 90%, further preferably at least 95% sequence identity therewith and having the ability to bind CD19 and induce T cell signaling.

According to the present disclosure, the CD19 antigen-recognizing and binding domain comprises a light chain variable region having a sequence set forth in one of SEQ ID NOs: 7-12, or a variant having at least 85%, preferably at least 90%, further preferably at least 95% sequence identity therewith and having the ability to bind CD19 and induce T cell signaling.

In the present disclosure, the applicant found that the affinity with hybridoma antibodies could be further improved by using the combinations of the 6 heavy chain and light chain sequences, and the killing effect is also significantly improved. The specific heavy chain variable region and light chain variable region of the CD19 antigen-recognizing and binding domain could be combined by any one of each heavy chain and light chain, which are shown in detail in following Table 1:

TABLE 1

| Sequence | Amino acid sequence |
|---|---|
| heavy chain (SEQ ID NO: 1) | QVQLVESGGGVVQPGRSLRLSCAASGFTFSRHGMHWVR QAPGKGLEWVAVIWYDGSNQYYVDSVKGRFTISRDNSKN TLDLQMNSLRVEDTAVYYCARRSITWYGGFDIWGQGTMV TVSSAQTTAPSVYPLAP |
| heavy chain (SEQ ID NO: 2) | QVQLVESGGGVVQPGRSLRLSCEASGFTFSRHGMHWVRQ APGKGLEWVAVIFYDGSQNYYADSVRGRFTISRDNSKNTL SLQMDSLRAEDTAVYYCARRSITWNGGFDIWGQGTMVT VSPAQTTAPSVYPLAP |

TABLE 1-continued

| Sequence | Amino acid sequence |
|---|---|
| heavy chain (SEQ ID NO: 3) | QVQLVESGGGVVQPGRSLRLSCAASGFTFSRHGMHWVR QAPGKGLEWVAVIWYDGSNKYYVDSVKGRFTISRDNSKN TLDLQMNSLRAEDTAVYYCARRSITWDGAFDIWGQGTM VTVSSAQTTAPSVYPLAP |
| heavy chain (SEQ ID NO: 4) | QVQLVESGGGVVQPGRSLRLSCAASGFTFSRHGMHWVR QAPGKGLEWVAVIYYDGSNKYYVDSVKGRFTISRDNSKN TLDLQMNSLRAEDTAVYYCARRSITWNGAFDIWGQGTM VTVSSAQTTAPSVYPLAP |
| heavy chain (SEQ ID NO: 5) | QVQLVESGGGVVQPGRSLRLSCAASGFTFSRHGMHWVR QAPGKGLEWVAVIWYDGSNKYYVDSVKGRFTISRDNSKN TLDLQMNSLRAEDTAVYYCARRSITWDGAFDIWGQGTM VTVSSAQTTAPSVYPLAP |
| heavy chain (SEQ ID NO: 6) | QVQLVESGGGVVQAGRSLRLSCAASGFTFSNYGIHWVRQ APGKGLEWVGVIWHDGSIKNYADFVKGRFTISRDNSEDTL YLQMNSLRAEDTAVYYCAREQGNYYGWGSYKAFDIWGQ GTMVTVSSAQTTAPSVYPLAP |
| light chain (SEQ ID NO: 7) | DIQMTQSPSTLSASVGDRVTITCRASQSISSWLAWYQQKP GKAPKLLIYKASSLESGVPPRFSGSGSGTEFTLTISSLQPDD FATYYCQQYNSAYTFGQGTKLEIK |
| light chain (SEQ ID NO: 8) | DIQMTQSPSTLSASVGDRVTITCRASQSISSWLAWYQQKP GKAPKLLIYKASSLESGVPSRFSGSGSGTEFTLAISSLQPDD FATYYCQQYNRFYTFGQGTKLEIK |
| light chain (SEQ ID NO: 9) | DIQMTQSPSTLSASVGDRVTISCRASQSISSWLAWYQQKP GKAPKLLIYKASSLESGVPSRFSGSGSGTEFTLTISSLQPDD FATYYCQQYNSAYTFGQGTKLEIK |
| light chain (SEQ ID NO: 10) | DIQMTQSPSTLSASVGDRVTISCRASQSISSWLAWYQQKP GKAPKLLIYKASSLESGVPSRFSGSGSGTEFTLTISSLQPDD FATYYCQQYNSAYTFGQGTKLEIK |
| light chain (SEQ ID NO: 11) | DIQMTQSPSTLSASVGDRVTVTCRASQSIRSWLAWYQQKP GKAPKLLIYKASSLESGVPSRFSGSGSGTEFTLTISSLQPDD FATYYCQQYNSAYTFGQGTKLEIK |
| light chain (SEQ ID NO: 12) | DIQLTQSPSFLSVFVGDRVTITCRASQGISNYLAWYQQKPG KAPELLLYATSTLQSGVPSRLSGSGSGTEFTLTLSSLQPEDF ATYYCQQVYSFPYTFGQGTKLEIK |

According to the present disclosure, the chimeric antigen receptor may be such that, for example: the heavy chain is SEQ ID NO: 1 and the light chain is SEQ ID NO: 7, the heavy chain is SEQ ID NO: 1 and the light chain is SEQ ID NO: 8, the heavy chain is SEQ ID NO: 1 and the light chain is SEQ ID NO: 9, the heavy chain is SEQ ID NO: 1 and the light chain is SEQ ID NO: 10, the heavy chain is SEQ ID NO: 1 and the light chain is SEQ ID NO: 11, the heavy chain is SEQ ID NO: 1 and the light chain is SEQ ID NO: 12, the heavy chain is SEQ ID NO: 2 and the light chain is SEQ ID NO: 7, the heavy chain is SEQ ID NO: 2 and the light chain is SEQ ID NO: 8, the heavy chain is SEQ ID NO: 2 and the light chain is SEQ ID NO: 9, the heavy chain is SEQ ID NO: 2 and the light chain is SEQ ID NO: 10, the heavy chain is SEQ ID NO: 2 and the light chain is SEQ ID NO: 11, the heavy chain is SEQ ID NO: 2 and the light chain is SEQ ID NO: 12, the heavy chain is SEQ ID NO: 3 and the light chain is SEQ ID NO: 7, the heavy chain is SEQ ID NO: 3 and the light chain is SEQ ID NO: 8, the heavy chain is SEQ ID NO: 3 and the light chain is SEQ ID NO: 9, the heavy chain is SEQ ID NO: 3 and the light chain is SEQ ID NO: 10, the heavy chain is SEQ ID NO: 3 and the light chain is SEQ ID NO: 11, the heavy chain is SEQ ID NO: 3 and the light chain is SEQ ID NO: 12, the heavy chain is SEQ ID NO: 4 and the light chain is SEQ ID NO: 7, the heavy chain is SEQ ID NO: 4 and the light chain is SEQ ID NO: 8, the heavy chain is SEQ ID NO: 4 and the light chain is SEQ ID NO: 9, the heavy chain is SEQ ID NO: 4 and the light chain is SEQ ID NO: 10, the heavy chain is SEQ ID NO: 4 and the light chain is SEQ ID NO: 11, the heavy chain is SEQ ID NO: 4 and the light chain is SEQ ID NO: 12, the heavy chain is SEQ ID NO: 5 and the light chain is SEQ ID NO: 7, the heavy chain is SEQ ID NO: 5 and the light chain is SEQ ID NO: 8, the heavy chain is SEQ ID NO: 5 and the light chain is SEQ ID NO: 9, the heavy chain is SEQ ID NO: 5 and the light chain is SEQ ID NO: 10, the heavy chain is SEQ ID NO: 5 and the light chain is SEQ ID NO: 11, the heavy chain is SEQ ID NO: 5 and the light chain is SEQ ID NO: 12, the heavy chain is SEQ ID NO: 6 and the light chain is SEQ ID NO: 7, the heavy chain is SEQ ID NO: 6 and the light chain is SEQ ID NO: 8, the heavy chain is SEQ ID NO: 6 and the light chain is SEQ ID NO: 9, the heavy chain is SEQ ID NO: 6 and the light chain is SEQ ID NO: 10, the heavy chain is SEQ ID NO: 6 and the light chain is SEQ ID NO: 11, or the heavy chain is SEQ ID NO: 6 and the light chain is SEQ ID NO: 12.

In some embodiments of the present disclosure, the amino acid sequence of the heavy chain variable region of the CD19 antigen-recognizing and binding domain comprises a variant having at least 85%, such as 85%, 86%, 88%, 90%, 92%, 95%, 98%, 99% identity with an amino acid sequence set forth in one of SEQ ID NOs: 1-6, and having the ability to bind CD19 and induce T cell signaling, preferably a variant having at least 90%, preferably at least 95% sequence identity, and having the ability to bind CD19 and induce T cell signaling.

In some embodiments of the present disclosure, the amino acid sequence of the light chain variable region of the CD19 antigen-recognizing and binding domain comprises a variant having at least 85%, such as 85%, 86%, 88%, 90%, 92%, 95%, 98%, 99% identity with an amino acid sequence set forth in one of SEQ ID NOs: 7-12, and having the ability to bind CD19 and induce T cell signaling, preferably a variant having at least 90%, preferably at least 95% sequence identity, and having the ability to bind CD19 and induce T cell signaling.

According to the present disclosure, the extracellular domain of the chimeric antigen receptor optionally further includes a signal peptide domain. The signal peptide domain is any one of a GM-CSF signal peptide, an IL-2 signal peptide, or a CD8a signal peptide.

According to the present disclosure, the chimeric antigen receptor further includes a CD3 signaling domain. The intracellular costimulatory signaling domain according to the present disclosure comprises any one or a combination of at least two of human CD28 intracellular region, human 4-1BB intracellular region, human TLR1 intracellular region, human TLR2 intracellular region, human TLR3 intracellular region, human TLR4 intracellular region, human TLR5 intracellular region, human TLR6 intracellular region, human TLR7 intracellular region, human TLR8 intracellular region, human TLR9 intracellular region, human TLR10 intracellular region, human DAP10 intracellular region, human CD27 intracellular region, human OX40 intracellular region, human CD30 intracellular region, human CD40 intracellular region, human PD-1 intracellular region, human CTLA-4 intracellular region, human TIM3 intracellular region, human LAG3 intracellular region, human TGFβ intracellular region, human ICOS intracellular region, human lymphocyte function associated antigen 1 intracellular region, human CD2 intracellular region, human CD7 intracellular region, human LIGHT intracellular region, human NKG2C intracellular region, human NKG2D intracellular region, human NKp46 intracellular region, human NKp30 intracellular region, human NKp44 intracellular region, human DNAM1 intracellular region, human B7-H3 intracellular region or human CD83 intracellular region, preferably any one or a combination of at least two of human CD28 intracellular region, human 4-1BB intracellular region, human TLR2 intracellular region or human DAP10 intracellular region×3, human DAP10 intracellular region×6, human DAP10 intracellular region×9 (the combination may be, for example, CD28-TLR2, 41BB-TLR2, 41BB-CD28, 41BB-CD28-TLR2, 41BB-CD28-DAP10×3, 41BB-TLR2-DAP10×3, CD28-TLR2-DAP10×3, TLR2-DAP10×3, CD28-DAP10×3, 41BB-DAP10×3, TLR2-DAP10×6, CD28-DAP10×6, 41BB-DAP10×9, TLR2-DAP10×9, CD28-DAP10×9 or 41BB-DAP10×9), preferably any one or a combination of at least two of human CD28 intracellular region, human 4-1BB intracellular region, human TLR2 intracellular region and human DAP10×3 intracellular region.

The optional transmembrane domain is preferably any one of CD3, CD8, CD28, OX40 or ICOS, further preferably CD28.

In a fourth aspect, the present disclosure provides a nucleic acid encoding the chimeric antigen receptor according to the third aspect.

In a fifth aspect, the present disclosure provides a chimeric antigen receptor-expressing cell into which the nucleic acid according to the fourth aspect is introduced.

According to the present disclosure, the cell is T cell or a cell population containing T cells.

In a sixth aspect, the present disclosure provides a method for preparing a chimeric antigen receptor-expressing cell according to the fifth aspect, which comprises the step of introducing the nucleic acid according to the fourth aspect into a cell.

Preferably, the cell is T cell or a cell population containing T cells.

In a seventh aspect, the present disclosure provides use of the scFv amino acid sequence according to the first aspect, the nucleotide sequence according to the second aspect, the chimeric antigen receptor according to the third aspect, the nucleic acid according to the fourth aspect or the chimeric antigen receptor-expressing cell according to the fifth aspect in the preparation of a medicament for treating a tumor.

Preferably, the tumor is CD19 positive malignant tumor and/or B cell malignant tumor.

In one embodiment of the present disclosure, the scFv amino acid sequence can be used to prepare antibodies for diagnosis and treatment of tumors.

In an eighth aspect, the disclosure provides a pharmaceutical composition for treating tumors, comprising any one or a combination of at least two of the scFv amino acid sequence according to the first aspect, the nucleotide sequence according to the second aspect, the chimeric antigen receptor according to the third aspect, the nucleic acid according to the fourth aspect or the chimeric antigen receptor-expressing cell according to the fifth aspect.

Preferably, the pharmaceutical composition further comprises an immunotherapy drug and/or a small molecule drug.

In the present disclosure, the immunotherapy drug may be, for example, any one or a combination of at least two of an anti-BCMA chimeric antigen receptor, an anti-CD20 chimeric antigen receptor, an anti-CD22 chimeric antigen receptor, an anti-CD20 monoclonal antibody, a BCR-ABL kinase inhibitor, an immune checkpoint inhibitor (PD-1/PD-L1 monoclonal antibody, CTLA-4 monoclone, TIM3 monoclonal antibody, LAG3 monoclonal antibody), a PD-1/PD-L1 chimeric antigen receptor, a CTLA-4 chimeric antigen receptor, a TIM3 chimeric antigen receptor or an LAG3 chimeric antigen receptor.

In the present disclosure, the pharmaceutical composition further comprises a small molecule chemical drug. For example, it may be any one or a combination of at least two of vincristine, daunorubicin, L-asparaginase, prednisone, pirarubicin, dexamethasone, asparaginase, adriamycin, cytarabine or pegaspargase, an MTOR inhibitor (Temsirolimus, Everolimus, Sirolimus), a proteasome inhibitor (Bortezomib, Carfilzomib, Ixazomib) or a histone deacetylase (HDAC) inhibitor (Belinostat, Vorinostat, Panobinostat).

It is noted that the term "intracellular costimulatory signaling domain" refers to any oligopeptide or polypeptide known to act as a domain that transmits signals in a cell to cause activation or inhibition of biological processes.

It is noted that the term "variant" refers to any variant that contains substitutions, deletions, or additions of one or several to more amino acids, provided that the variant substantially retains the same function as the original sequence.

Compared with the prior art, the present disclosure has the following beneficial effects:

The CD19 antigen-recognizing and binding domain of the present disclosure has been humanized, which may reduce the occurrence of xenoimmune rejection without affecting the ability to recognize target antigens on tumor cells, thereby resulting in an improved duration of CAR-T cells in the human body, an enhanced immune ability to monitor tumor cells, a reduced tumor recurrence rate, and a corresponding extended complete remission period in patients.

BRIEF DESCRIPTION OF THE DRAWINGS

FIG. 1 shows the results of binding of hybridoma antibodies to CD19-his, wherein

FIG. 4 shows the affinity analysis of CD19 antibodies with different antigens, wherein

DETAILED DESCRIPTION

Figure 1A:
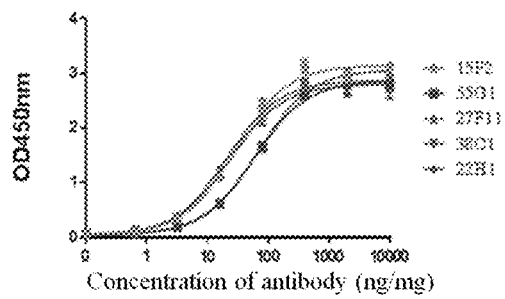
FIG. 1A shows the results of binding of 15F2, 55G1, 27F11, 38C1 and 22H1 to hybridoma antibodies.
Figure 1B:
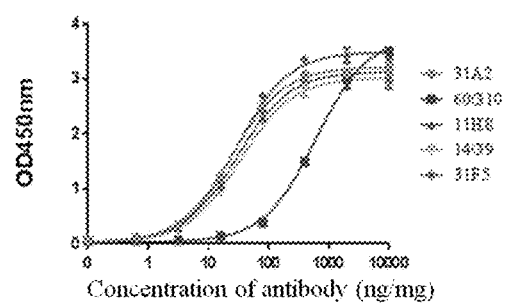
FIG. 1B shows the results of binding of 31A2, 60G10, 11H8, 14G9 and 31F5 to hybridoma antibodies.
Figure 1C:
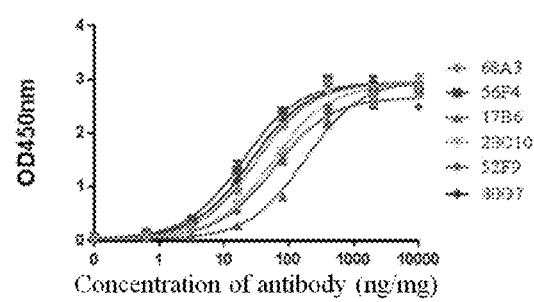
FIG. 1C shows the results of binding of 68A3, 56F4, 17B6, 28C10, 52F9 and 80G7 to hybridoma antibodies.
Figure 1D:
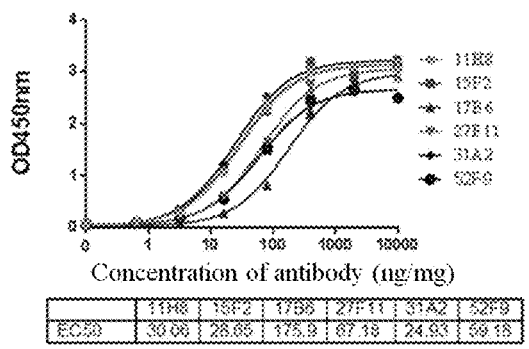
FIG. 1D shows the results of binding of 11H8, 15F2, 17B6, 27F11, 31A2 and 52F9 to hybridoma antibodies.

The present disclosure will be described in further detail with reference to the following examples. Those skilled in the art should be understood that these examples are merely provided to assist in understanding the present disclosure, and are not intended to specifically limit the present disclosure.

Construction of CAR Plasmid

As mentioned above, the CAR molecule includes an extracellular region, a transmembrane region, and an intracellular region. Therefore, the construction steps of the CAR plasmid for the following examples include:

first, obtaining each gene DNA required for the CAR plasmid through gene synthesis, including: anti-CD19 antibody immunoglobulin heavy and light chain variable region sequences, a CD28 transmembrane signal region sequence, a TLR1 signal transmission region sequence, a TLR2 signal transmission region sequence, a DAP10×3 signal transmission region sequence, and a CD3 signal transmission region sequence;

then, connecting the required gene sequences synthesized above in tandem through steps such as enzyme digestion and ligation to obtain the CAR molecule of the present disclosure.

Materials:

hCD19-fc was purchased from ACRO Biosystems Cat #CD9-H5259.

hCD19-his was purchased from ACRO Biosystems Cat #CD9-H52H2.

EXAMPLES

Example 1: Preparation and Identification of hCD19 Proteins

Hcd19 proteins were prepared as following steps:

hCD19-fc: the human CD19 recombinant protein (Accession #AAH06338) was expressed in HEK293 cells. Pro20-Lys291 sequence (tagged with Fc at C-terminus) of human CD19 gene coding region was selected for transfection. The purified protein was identified by SDS-PAGE gel.

hCD19-his: the human CD19 recombinant protein (Accession #P15391-1) was expressed in HEK293 cells. Pro20-Lys291 sequence (tagged with His at C-terminus) of human CD19 gene coding region was selected for transfection. The purified protein was identified by SDS-PAGE gel.

Example 2: Preparation of Antibodies (I) Antigen Conjugation and Immunization (1) The hCD19-Fc recombinant protein was immune-conjugated with various MabSpace immune-enhancing peptides, and the quality of the conjugated protein was controlled by SDS-PAGE gel detection.

(2) Freund's complete adjuvant (Pierce, Cat #77140) was added to the above conjugated hCD19-Fc protein at a ratio of 1:1 for emulsification, and then immunized H2L2 mice by subcutaneous and intraperitoneal injection, respectively. H2L2 mice were produced by Harbour BioMed, and carried genes for human variable regions and rat constant regions, without endogenous mouse antibody genes. Additional immunization was performed with CpG (Cytosine-phosphorothioate-Guanine) and alum to preserve the natural structure of the protein. Mouse sera were collected after the first immunization and after immunity emerged (at least once every 2 weeks), and the anti-hCD19 titer in the antiserum was then analyzed by ELISA.

(II) Fusion 4 days before fusion, unconjugated hCD19-His protein in PBS solution was intraperitoneally injected into each mouse. On the day of fusion, the mouse spleen was obtained aseptically and prepared into single-cell suspension by shearing, grinding, and filtration. Red blood cells were lysed, and the spleen cells were washed with DMEM (Gibco). Live myeloma cells (SP2/0) in the logarithmic growth phase were mixed with mouse spleen cells at a ratio of 1:4 and washed 2 times before fusing with PEG (polyethylene glycol). After fusion, the cells were washed with DMEM medium and resuspended with 10% FBS+HFCs (hydrofluorocarbons)+OPI+1×HAT cell growth medium. The resuspended cells were placed in a 96-well cell culture plate with 200 µl cell growth medium per well, and incubated overnight at 37° C. in a humidified incubator with 10% carbon dioxide. During the culture for 7 days, the supernatant of the hybridoma culture medium was pipetted out every 2-3 days (reserved for antibody screening) and replaced with fresh culture medium.

(III) Antibody Screening by ELISA

1 µg/ml of human CD19-His was added to a 96-well plate at 100 µl per well, and incubated at 4° C. overnight. After washing, 100 µl of hybridoma culture supernatant was added to completely combine with human CD19-His. HRP (horseradish peroxidase)-labeled goat anti-rat Fc antibody was added to detect the bound CD19 antibody. After reacting with TMB and stopping the reaction by H2SO4, the plate was read with Thermo Multiscan FC (450 nM). Positive hybridoma cells detected by ELISA were continued to be cultured for further identification and analysis.

Example 3 Subcloning Positive Hybridoma Cells and Small-Scale Production of Antibodies (I) Subcloning Positive Hybridoma Cells (1) The ELISA-positive hybridoma cells were gradiently diluted in 96-well plates to select cells with ideal affinity and blocking activity. After culturing for 7 days, a cell clonal mass was formed, and the supernatant was collected, which was further screened based on antigen binding ability according to the method in Example 2.

(2) Based on the screening results, the clones with the highest antigen affinity were selected and cultured in hybridoma growth medium. After 7 days, the supernatant of the screened hybridoma cell culture fluid was tested again for antigen binding ability. The subcloning screening test was performed at least twice, until at least 90 wells (96 well plates).

(3) When more than 90 wells showed positive binding signals, two clones with the highest antigen binding activity were identified and transferred to medium in 24-well plates, where they were allowed to grow for another 2 days. Once the 24-well plates were confluent, the cells were transferred to 6-well plates. After 5 days of incubation, some cells were frozen. The rest cells were transferred to a flask and allowed to expand. Once the flasks were confluent, half of the cells were frozen (3 bottles for each clone) for additional backup, and the other half were allowed to further expand in medium to produce antibodies. The isotype was determined by standard methods.

(II) Small-Scale Production of Monoclonal Antibodies (1) The hybridoma cells were inoculated in roller bottles and incubated in 200-300 ml of hybridoma medium (Invitrogen) for 14 days. CD19 monoclonal antibodies (mAbs) were purified from hybrid cell culture as follows: all of the purification processes were carried out at room temperature, and various monoclonal antibodies were purified by affinity chromatography.

(2) The host cell culture fluid (CCF) was centrifuged to remove cell debris, and then the CCF supernatant was filtered, diluted, and then loaded onto protein G chromatography medium in the form of column, protein G high performance (Bio-Rad) and equilibrium.

(3) After loading, the protein G column was washed until the absorbance at 280 nm returned to baseline. The CD19 monoclonal antibodies were eluted with pH 2.5 glycine, and 1 M Tris (per 1 mL of eluent) was then immediately added to neutralize. The absorbance of the eluent at 280 nm was taken as a control. The components containing protein were collected and the proteins were pooled.

(4) After the purification, the CD19 monoclonal antibodies dialyzed through a 10,000 MWCO membrane (Pierce synovial lysis apparatus or dialysis tube) was prepared with PBS. After the preparation, the CD19 monoclonal antibodies were filtered.

Example 4 Binding Analysis of the Purified CD19 Antibodies by ELISA

The antibodies were screened by ELISA according to Example 2. Briefly, 0.5 µg/ml of hCD19-His (ACRO) were spread and incubated. The purified antibodies were serially diluted to bind the incubated antigen. The binding signal of each antibody could be detected with HRP-labeled goat anti-rat Fc antibody.

Graphpad Prism software was used to calculate the fitting data. The summary of EC50 of the antibodies is shown in FIG. 1 and Table 1:

TABLE 1

| Antibody | EC50 (ng/ml) | Antibody | EC50 (ng/ml) |
|---|---|---|---|
| 16B7 | 60.5 | 55D9 | 25.9 |
| 21F1 | 46.6 | 16G6 | 31.5 |
| 32G7 | 58.8 | 80G5 | 24.6 |
| 21G5 | 60.0 | 68A3 | 31.2 |
| 22A3 | 40.9 | 31F5 | 119.7 |
| 12D1 | 57.1 | 56F4 | 19.3 |
| 15F2 | 28.7 | 17B6 | 175.9 |
| 55G1 | 59.2 | 28C10 | 56.1 |
| 27F11 | 67.2 | 52F9 | 59.2 |
| 51E9 | 2108.0 | 80G7 | 25.8 |
| 38C1 | 20.8 | 30E7 | 5286.0 |
| 22H1 | 23.6 | 44C9 | 224.2 |
| 31A2 | 24.9 | 26C2 | 295.0 |
| 29C12 | ~215395 | 21D5 | 32177.0 |
| 27B9 | 46.8 | 46E6 | 2.494e+006 |
| 44C12 | 75.9 | 47D8 | 14877.0 |
| 60G10 | 608.8 | 45E9 | 446.1 |
| 11H8 | 30.1 | 40D3 | 72.1 |
| 14G9 | 33.9 | 24E10 | 129.0 |
| 31F5 | 29.2 | 19D6 | 73.7 |
| 16D4 | 33.0 | 15H10 | 30791.0 |
| 31G6 | 26.8 | 31F11 | 238.9 |
| 22G11 | 66.6 | | |

As shown in FIG. 1 and Table 1, all of the antibodies have a certain affinity for hCD19-His, though the affinity for hCD19-His is different. Therefore, selecting these antibodies as the extracellular domain of the chimeric antigen receptor can achieve the function of recognizing CD19.

Example 5: Binding to an Epitope by Fortiebio Method

The first CD19 antibody was diluted in kinetic buffer (PBS) on loading column of microplate (Greiner Bio-one), 250 μl/well, and hCD19-his was diluted in kinetic buffer (PBS) on association column, 250 μl/well. The AHC sensor was placed in the first baseline column to get the first baseline, and then placed in the loading column for 300 seconds to capture the first CD19 antibody. Thereafter the sensor was placed in the second baseline column to get the second baseline; and then put them in the association column for 300 seconds to allow the CD19/1 CD19 antibody to be fully associated. The sensor was then placed in the second CD19 antibody column for 300 seconds to allow the second CD19 antibody to compete/not compete with the first Ab. ForteBio (Octet96) was used to analyze the data. The results are shown in FIG. 2 and Table 2 as follows:

TABLE 2

| Bin 1 | | Bin 2 | |
|---|---|---|---|
| 27F11 | 22A3 | 56F4 | 55G1 |
| 17B6 | 44C12 | 38C1 | 52F9 |
| 31A2 | 16B7 | 22G11 | |
| 11H8 | 55D9 | 51E9 | |
| 27B9 | 21F1 | 22H1 | |
| 15F2 | 68A3 | 60G10 | |
| 28C10 | 16G6 | 31G6 | |
| 21G5 | 80G7 | 80G5 | |
| 32G7 | 31F5 | 14G9 | |
| 16D4 | 12D1 | | |

Figure 2:
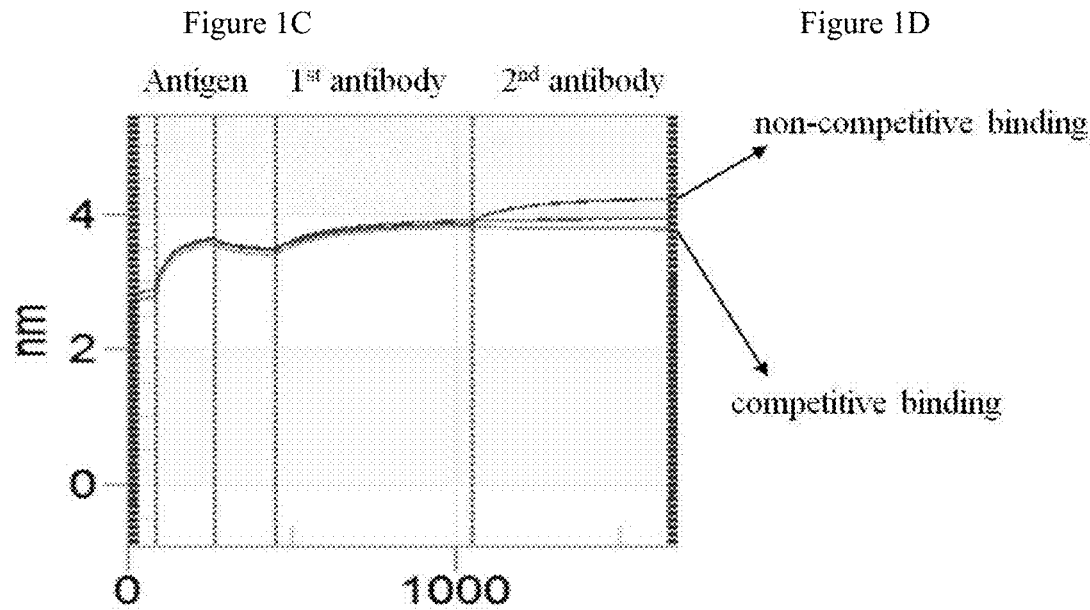
FIG. 2 is a graph showing the results of binding of an CD19 antibody to an epitope.

As shown in FIG. 2 exemplarily, if the second CD19 Ab cannot bind to CD19, it means that it has a similar epitope to the first one and competes therewith; if the second antibody can bind to the first without being affected by the first antibody and without resulting in any impact, then their epitopes are different and non-competitive. Based on these results, the antibodies are divided into two groups according to the competition results. The two groups have different epitopes. The results are shown in Table 2. Most of the antibodies belong to Bin1 except for only two of them belong to Bin2.

Example 6: Binding Analysis of the Purified CD19 Antibodies with Flow Cytometry (FACS)

Figure 3:
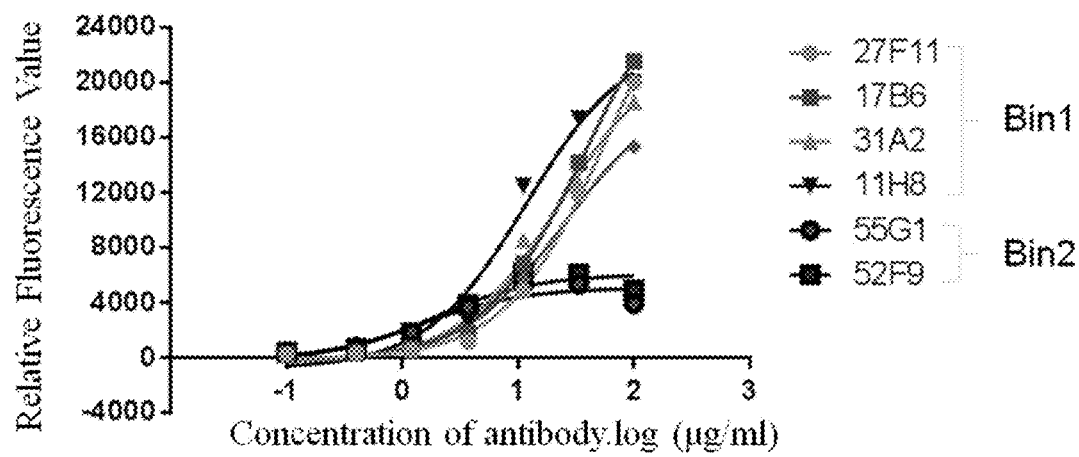
FIG. 3 shows the binding analysis of CD19 antibodies with the best affinity.

The CD19-expressing tumor cells Nalm6 in logarithmic growth phase were collected and resuspended in PBS at a cell density of $10^5$/well, 100 μl/well. The diluted CD19 antibodies were added into the well and incubated at 4° C. for 1 hour. The cells were washed three times with flow cytometry wash buffer. Anti-rat IgG-Alexa Fluor 647 (Abcam, Cat #ab150163) was added and incubated at 4° C. for 1 hour. The cells were washed three times with flow cytometry wash buffer. The samples were analyzed by flow cytometry. The results are shown in FIG. 3 and Table 3, as follows:

TABLE 3

| Antibody | Maximum mean fluorescence intensity (30 μg/ml) | Antibody | Maximum mean fluorescence intensity (30 μg/ml) |
|---|---|---|---|
| 16B7 | 11521 | 55D9 | 10375 |
| 21F1 | 9938 | 16G6 | 8526 |
| 32G7 | 16627 | 80G5 | 13145 |
| 21G5 | 18486 | 68A3 | 9731 |
| 22A3 | 12157 | 31F5 | 6388 |
| 12D1 | 5272 | 56F4 | 4961 |
| 15F2 | 21748 | 17B6 | 25457 |
| 55G1 | 5718 | 28C10 | 18946 |
| 27F11 | 30021 | 52F9 | 5160 |
| 51E9 | 2593 | 80G7 | 8505 |
| 38C1 | 3427 | 30E7 | 2791 |
| 22H1 | 2111 | 44C9 | 10544 |
| 31A2 | 24698 | 26C2 | 10899 |
| 27B9 | 22315 | 21D5 | 4746 |
| 44C12 | 11995 | 46E6 | 1990 |
| 60G10 | 1868 | 47D8 | 1390 |
| 11H8 | 23266 | 45E9 | 9877 |
| 14G9 | 12290 | 40D3 | 6619 |
| 31F5 | 7472 | 24E10 | 8235 |
| 16D4 | 15146 | 19D6 | 10357 |
| 31G6 | 13855 | 15H10 | 4284 |
| 22G11 | 3340 | 31F11 | 4996 |

As shown in Table 3, 27F11, 17B6, 31A2, 11H8, 27B9 and 15F2 have the highest binding signal to Nalm6. The MFI (mean fluorescence intensity) of the background (anti-rat IgG-Alexa Fluor 647) is about 450. As shown in FIG. 3, the binding curves of the antibodies of the two Bin are different: 27F11, 17B6, 31A2, and 11H8 of Bin1 have higher binding signal and higher EC50; and 55G1 and 52F9 of Bin2 have lower signal and lower EC50.

Example 7: Specific Binding (ELISA)

According to the method described in Example 4, 0.5 μg/ml of hCD19-His, hVISTA-his, hPD-L1, hCD40, h41BB and hLAG3 were spread and incubated respectively, and 2 μg/ml of purified antibodies were added to bind the incubated antigen. The binding signal of each antibody could be detected with HRP-labeled goat anti-rat Fc antibody. The results are shown in FIG. 4.

Figure 4A:
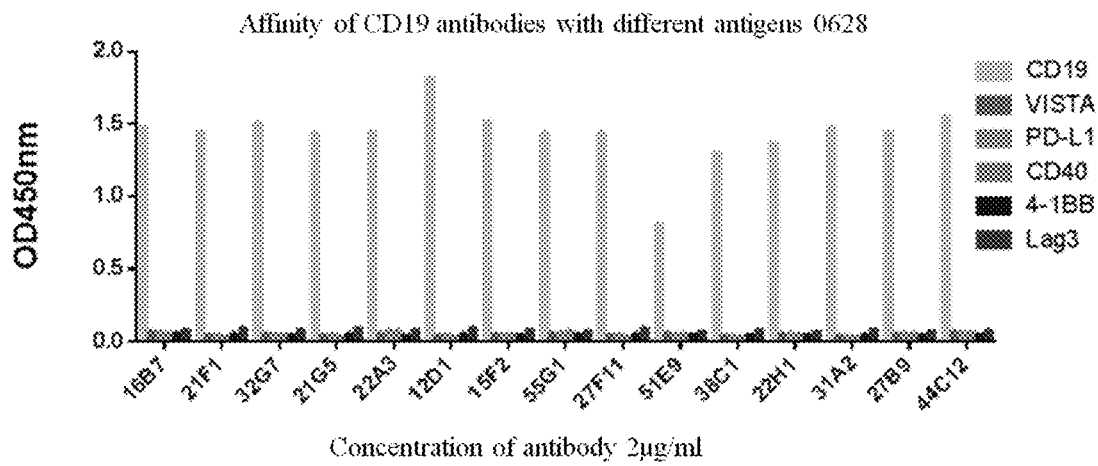
FIG. 4A shows the results of binding of antigens to CD19 antibodies for 16B7, 21F1, 32G7, 21G5, 22A3, 12D1, 15F2, 55G1, 27F11, 51E9, 38C1, 22H1, 31A2, 27B9 and 44C12.
Figure 4B:
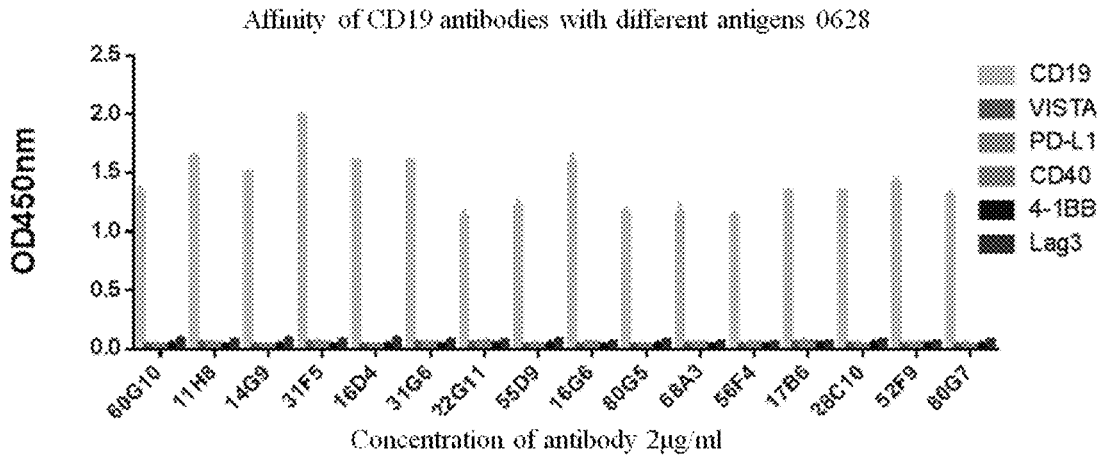
FIG. 4B shows the results of binding of antigens to CD19 antibodies for 60G10, 11H8, 14G9, 31F5, 16D4, 31G6, 32G11, 55D9, 16G6, 80G5, 68A3, 56F4, 17B6, 28C10, 52F9 and 80G7.

As shown in FIG. 4, all of these antibodies: 16B7, 21F1, 32G7, 21G5, 22A3, 12D1, 15F2, 55G1, 27F11, 51E9, 38C1, 22H1, 31A2, 27B9, 44C12, 60G10, 11H8, 14G9, 31F5, 16D4, 31G6, 32G11, 55D9, 16G6, 80G5, 68A3, 56F4, 17B6, 28C10, 52F9 and 80G7 did not cross-react with other antigens (except hCD19), indicating that the antibodies had good specificity for CD19.

Example 8: Gene Cloning and Sequencing of Hybrid Antibodies

The light chain and heavy chain variable region sequences of rat anti-human CD19 antibody were obtained by polymerase chain reaction (PCR) amplification. Total RNA was extracted from hybridoma cells expressing 11H8, 17B6, 31A2, 27F11, 15F2, 19D6, and 52F9 respectively using RNA extraction kit (TAKARA), and cDNA (Oligo DT primer) was synthesized using PrimeScript II first-strand cDNA synthesis kit (TAKARA). A degenerate forward primer and a reverse primer (determined by the antibody isotype) were used to clone the heavy chain variable region of IgG gene, and mK-F forward primer and cK-R reverse primer were used to clone the light chain variable region. The band produced for each antibody was cloned into a trans-5a cloning vector, and the DNA of more than 10 clones was measured with a DNA star sequencing instrument.

Sequencing results show that the amino acid sequence of 15F2 and 19D6 are the same, so this clone is named 15F2. Sequence results are shown in Table 4, as follows:

TABLE 4

| Sequence | | Amino acid sequence |
|---|---|---|
| 11H8 | heavy chain (SEQ ID NO: 1) | QVQLVESGGGVVQPGRSLRLSCAASGFTFSRH GMHWVRQAPGKGLEWVAVIWYDGSNQYYV DSVKGRFTISRDNSKNTLDLQMNSLRVEDTAV YYCARRSITWYGGFDIWGQGTMVTVSSAQTT APSVYPLAP |
| 11H8 | light chain (SEQ ID NO: 7) | DIQMTQSPSTLSASVGDRVTITCRASQSISSWL AWYQQKPGKAPKLLIYKASSLESGVPPRFSGS GSGTEFTLTISSLQPDDFATYYCQQYNSAYTFG QGTKLEIK |
| 17B6 | heavy chain (SEQ ID NO: 2) | QVQLVESGGGVVQPGRSLRLSCEASGFTFSRH GMHWVRQAPGKGLEWVAVIFYDGSQNYYAD SVRGRFTISRDNSKNTLSLQMDSLRAEDTAVY YCARRSITWNGGFDIWGQGTMVTVSPAQTTA PSVYPLAP |
| 17B6 | light chain (SEQ ID NO: 8) | DIQMTQSPSTLSASVGDRVTITCRASQSISSWL AWYQQKPGKAPKLLIYKASSLESGVPSRFSGS GSGTEFTLAISSLQPDDFATYYCQQYNRFYTFG QGTKLEIK |
| 31A2 | heavy chain (SEQ ID NO: 3) | QVQLVESGGGVVQPGRSLRLSCAASGFTFSRH GMHWVRQAPGKGLEWVAVIWYDGSNKYYV DSVKGRFTISRDNSKNTLDLQMNSLRAEDTAV YYCARRSITWDGAFDIWGQGTMVTVSSAQTT APSVYPLAP |
| 31A2 | light chain (SEQ ID NO: 9) | DIQMTQSPSTLSASVGDRVTISCRASQSISSWL AWYQQKPGKAPKLLIYKASSLESGVPSRFSGS GSGTEFTLTISSLQPDDFATYYCQQYNSAYTFG QGTKLEIK |
| 27F11 | heavy chain (SEQ ID NO: 4) | QVQLVESGGGVVQPGRSLRLSCAASGFTFSRH GMHWVRQAPGKGLEWVAVIYYDGSNKYYVD SVKGRFTISRDNSKNTLDLQMNSLRAEDTAVY YCARRSITWNGAFDIWGQGTMVTVSSAQTTA PSVYPLAP |
| 27F11 | light chain (SEQ ID NO: 10) | DIQMTQSPSTLSASVGDRVTISCRASQSISSWL AWYQQKPGKAPKLLIYKASSLESGVPSRFSGS GSGTEFTLTISSLQPDDFATYYCQQYNSAYTFG QGTKLEIK |
| 15F2 | heavy chain | QVQLVESGGGVVQPGRSLRLSCAASGFTFSRH GMHWVRQAPGKGLEWVAVIWYDGSNKYYV |

TABLE 4-continued

| Sequence | | Amino acid sequence |
|---|---|---|
| | (SEQ ID NO: 5) | DSVKGRFTISRDNSKNTLDLQMNSLRAEDTAV YYCARRSITWDGAFDIWGQGTMVTVSSAQTT APSVYPLAP |
| 15F2 | light chain (SEQ ID NO: 11) | DIQMTQSPSTLSASVGDRVTVTCRASQSIRSW LAWYQQKPGKAPKLLIYKASSLESGVPSRFSG SGSGTEFTLTISSLQPDDFATYYCQQYNSAYTF GQGTKLEIK |
| 52F9 | heavy chain (SEQ ID NO: 6) | QVQLVESGGGVVQAGRSLRLSCAASGFTFSN YGIHWVRQAPGKGLEWVGVIWHDGSIKNYA DFVKGRFTISRDNSEDTLYLQMNSLRAEDTAV YYCAREQGNYYGWGSYKAFDIWGQGTMVT VSSAQTTAPSVYPLAP |
| 52F9 | light chain (SEQ ID NO: 12) | DIQLTQSPSFLSVFVGDRVTITCRASQGISNYLA WYQQKPGKAPELLLYATSTLQSGVPSRLSGSG SGTEFTLTLSSLQPEDFATYYCQQVYSFPYTFG QGTKLEIK |

Example 9 Production of Fully Humanized Antibodies

After sequencing analysis and confirmation, the variable regions of each of the above genes were cloned into recombinant expression vectors, for example, a light chain variable region sequence (VL) fused with a human immunoglobulin IgG kappa constant region was cloned into pcDNA3.1 (+) vector, and a heavy chain variable region sequence (VH) fused with a human IgG1 constant region was cloned into pcDNA3.1 (+) vector, for producing and purifying the antibodies, respectively.

Example 10 Expression and Purification of Recombinant Fully Humanized Antibodies The expression and purification of recombinant antibody proteins include the following steps:

(1) ExpiCHO cells at a density of $(5-6) \times 10^6$ cells/ml were cultured with ExpiCHO expression medium, and equal amounts of heavy chain vectors and light chain vectors were then transfected into the ExpiCHO cells by using an ExpiCHO transfection kit with the vector DNA at a final concentration of 1.0 μg/ml. The transfected cells were cultured in a shaking flask at 125 rpm in an incubator with 8% carbon dioxide at 37° C., and ExpiCHO medium was added 18-22 h after the transfection.

(2) The mixed culture of cells was collected on the 10th day. The Harvest Cell Culture Fluid (HCCF) was obtained by centrifugation, which was then added to rProteinA column (G.E. Healthcare) and washed with PBS. The IgG antibodies were eluted with a solution (pH 3.2) containing 20 mM citric acid. Finally, the eluted antibody proteins were neutralized and stored at −80° C. for reservation. The produced antibodies were analyzed by SDS-PAGE and size exclusion chromatography (TSKgel G3000SWXL, TOSOH) to determine the purity.

Example 11: Binding Characteristics of Purified Humanized Antibodies (I) Binding to Human CD19 Protein by ELISA According to the method described in Example 4, 0.5 μg/ml of hCD19-His was spread and incubated. The fully humanized antibodies were serially diluted and added to bind the incubated antigen. The binding signal of each antibody could be detected with HRP-labeled goat anti-rat Fc antibody. The results are shown in FIG. 5 and Table 5, as follows:

TABLE 5

|  | 11H8 | 15F2 | 17B6 | 27F11 | 31A2 | 52F9 |
|---|---|---|---|---|---|---|
| EC50 | 2.629 | 3.779 | 4.522 | 3.995 | 4.458 | 7.916 |

Figure 5:
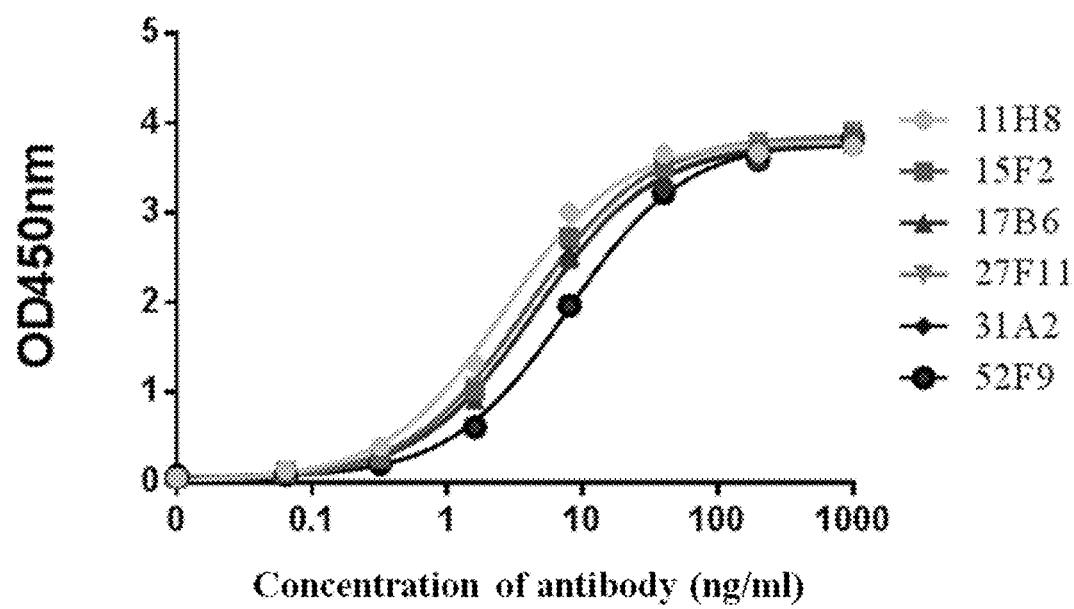
FIG. 5 is a graph showing the results of binding of CD19 fully humanized antibodies to CD19-his.

As shown in FIG. 5 and Table 5, the EC50 of each antibody is about 2-8 ng/ml, indicating that the binding affinity of the antibodies is very high.

(II) Detection of Binding Between Antibodies with Nalm6 Cells by Flow Cytometry FACS According to the method described in Example 6, Nalm6 cells in logarithmic growth phase were collected and centrifuged, then resuspended and diluted with PBS to a cell density of $10^5/100$ μl/well. The diluted fully humanized antibodies were added and incubated at 4° C. for 1 hour. The cells were washed three times with flow cytometry wash buffer. Anti-human IgG-Cy5 (Abcam, Cat #ab97172) was added and incubated at 4° C. for 1 hour. The cells were washed three times with flow cytometry wash buffer. The samples were analyzed by flow cytometry. The results are shown in FIG. 6 and Table 6, as follows:

TABLE 6

|  | 11H8 | 15F2 | 17B6 | 27F11 | 31A2 | 52F9 |
|---|---|---|---|---|---|---|
| EC50 | 2.056 | 4.161 | 5.026 | 2.809 | 4.763 | 1.567 |

Figure 6:
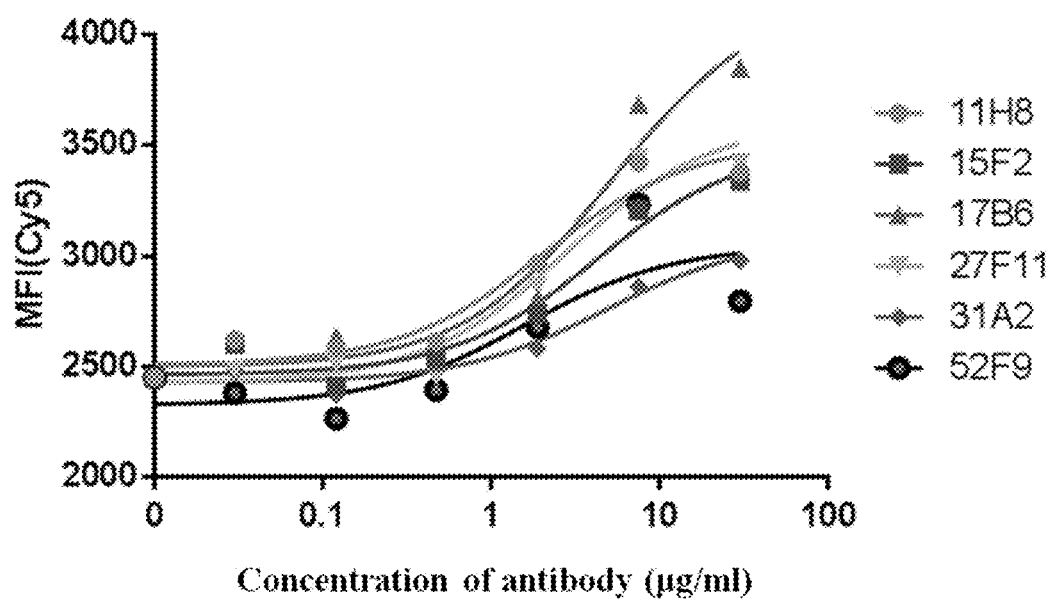
FIG. 6 is a graph showing the results of binding of CD19 fully humanized antibodies to Nalm6/GL.

As shown in FIG. 6 and Table 6, these fully humanized antibodies: 11H8, 15F2, 17B6, 27F11, 31A2 and 52F9 bind to CD19 expressed by Nalm6 cells in a dose-dependent manner, in which 17B6 has the highest binding signal.

Figure 7:
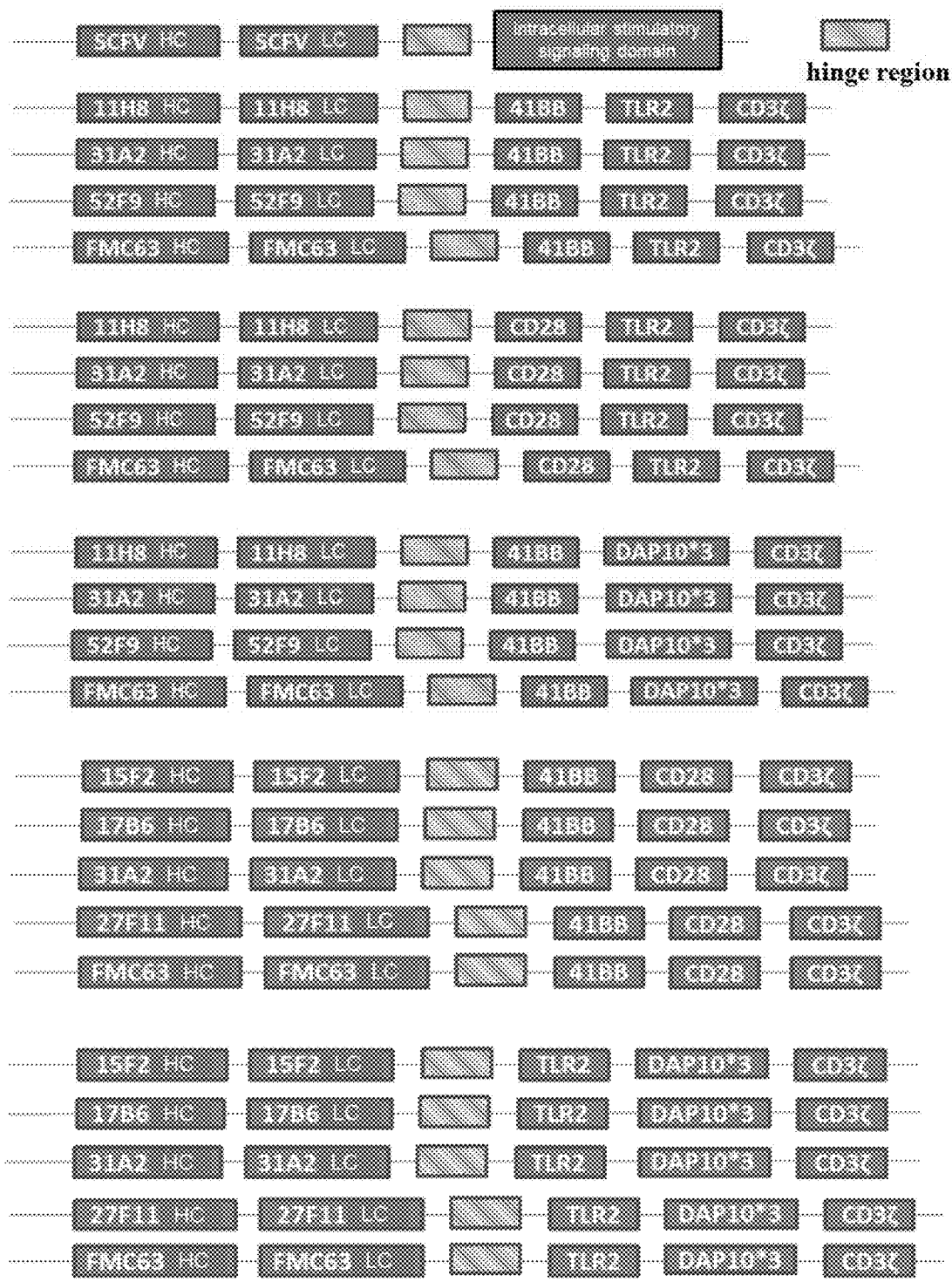
FIG. 7 is a diagram showing the molecular structures of chimeric antigen receptor CAR 19SCFV.
Figure 8:
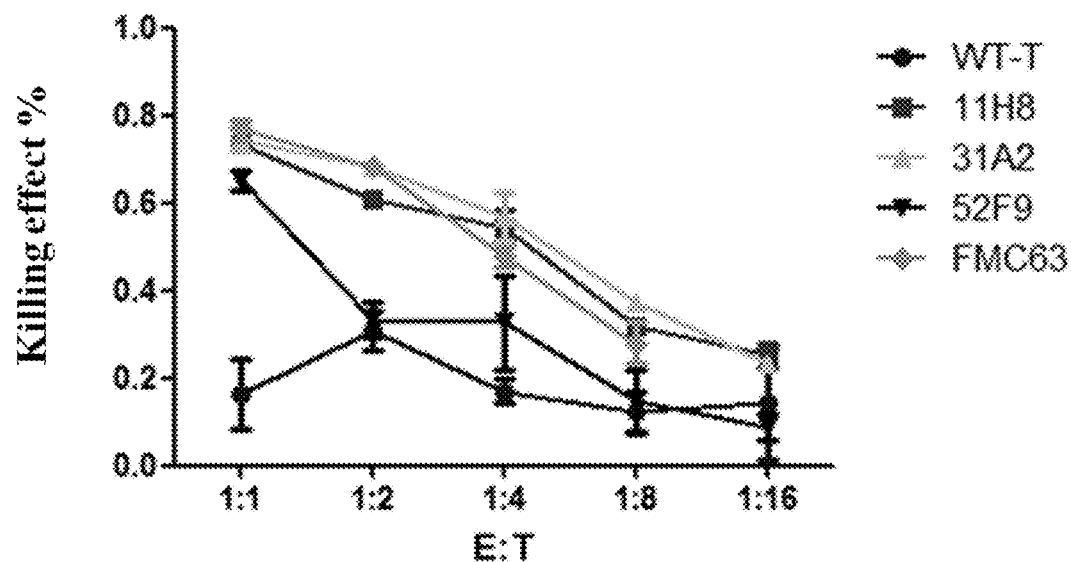
FIG. 8 shows targeting and killing of CD19+ lymphoma cell line RAJI in vitro by CAR (11H8/31A2/52F9/FMC63)-41BB-TLR2-CD3ζ T cells.
Figure 9:
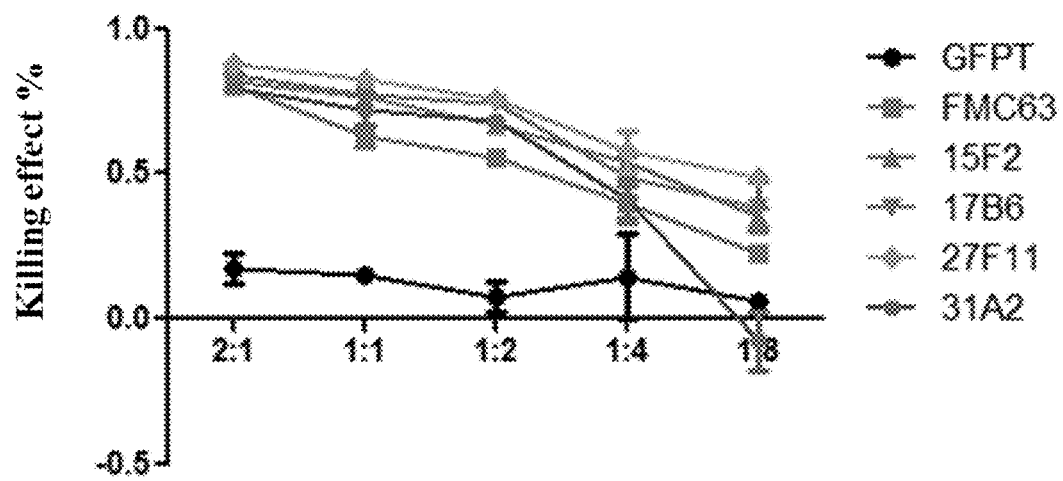
FIG. 9 shows targeting and killing of CD19+ lymphoma cell line RAJI in vitro by CAR (15F2/17B6/27F11/31A2/FMC63)-41BB-TLR2-CD3ζ T cells.
Figure 10:
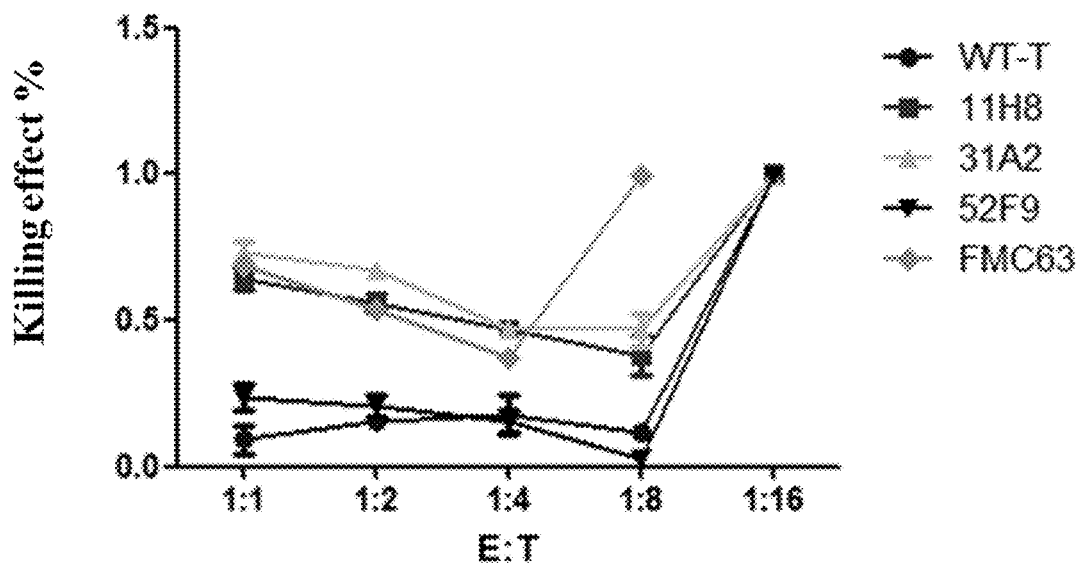
FIG. 10 shows targeting and killing of CD19+ leukemia cell line NALM6 in vitro by CAR (11H8/31A2/52F9/FMC63)-CD28-TLR2-CD3ζ T cells.
Figure 11:
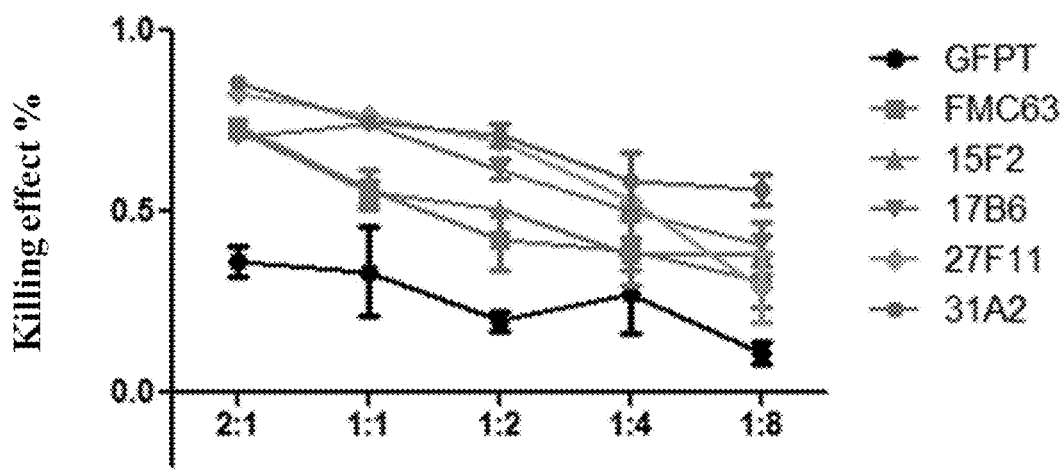
FIG. 11 shows targeting and killing of CD19+ leukemia cell line NALM6 in vitro by CAR (15F2/17B6/27F11/31A2/FMC63)-41BB-DAP10×3-CD3ζ T cells.
Figure 12:
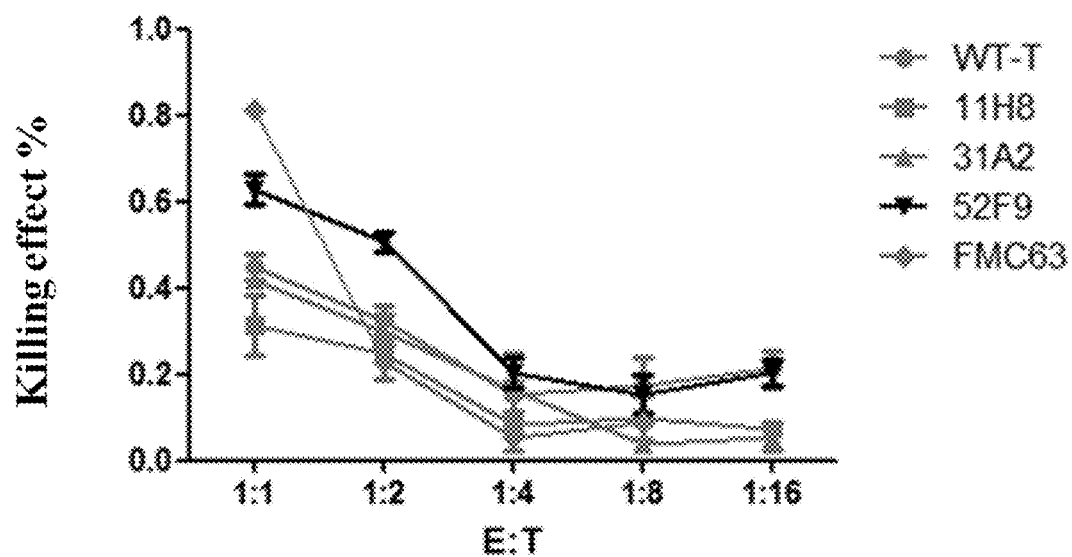
FIG. 12 shows the results of killing acute myeloid leukemia cell line AML3 in vitro by CAR (11H8/31A2/52F9/FMC63)-41BB-TLR2-CD3ζ T cells.
Figure 13:
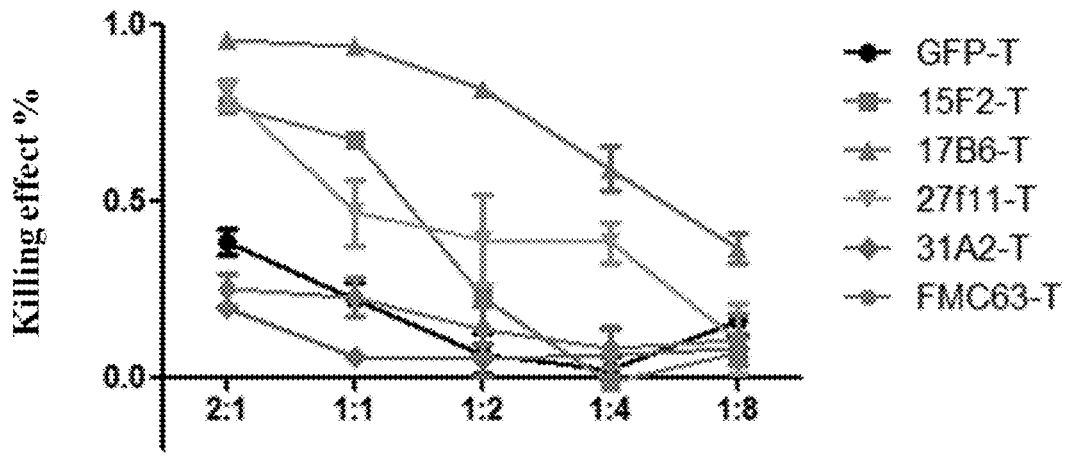
FIG. 13 shows the results of killing acute myeloid leukemia cell line AML3 in vitro by CAR (15F2/17B6/27F11/31A2/FMC63)-41BB-CD28-CD3ζ T cells.
Figure 14:
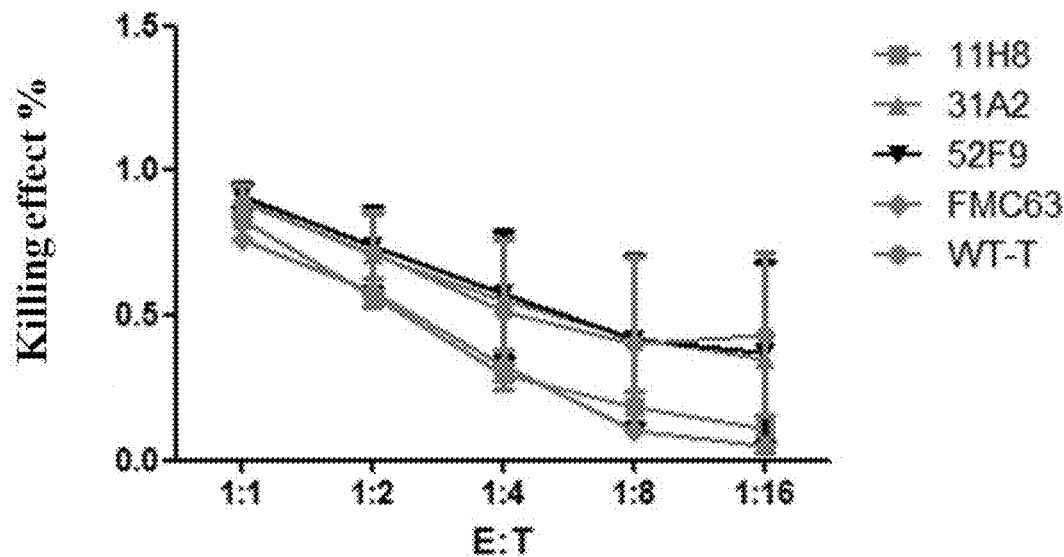
FIG. 14 shows the results of killing lung cancer cell line A549 in vitro by CAR (11H8/31A2/52F9/FMC63)-41BB-TLR2-CD3ζ T cells.
Figure 15:
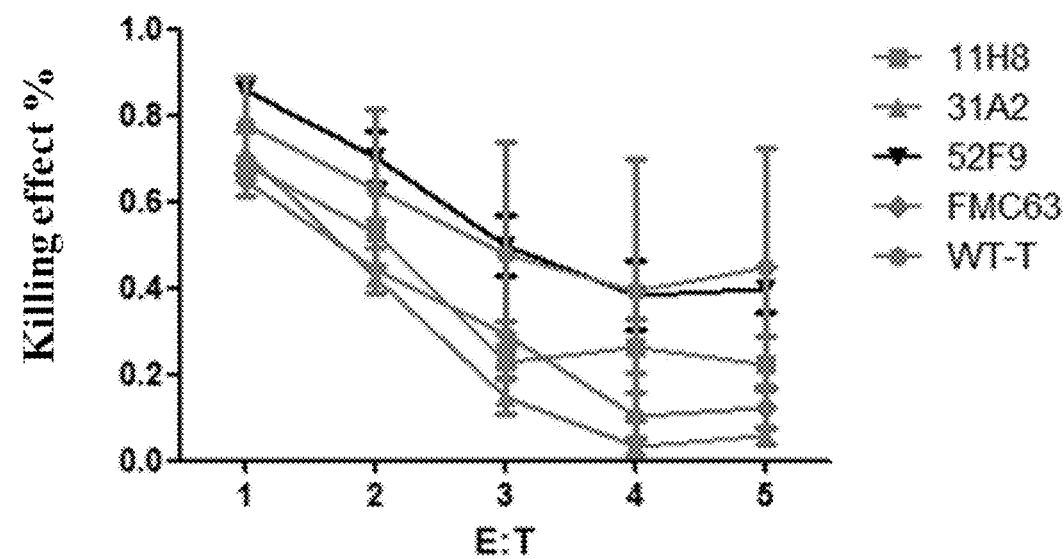
FIG. 15 shows the results of killing lung cancer cell line H460 in vitro by CAR (11H8/31A2/52F9/FMC63)-CD28-TLR2-CD3ζ T cells.
Figure 16:
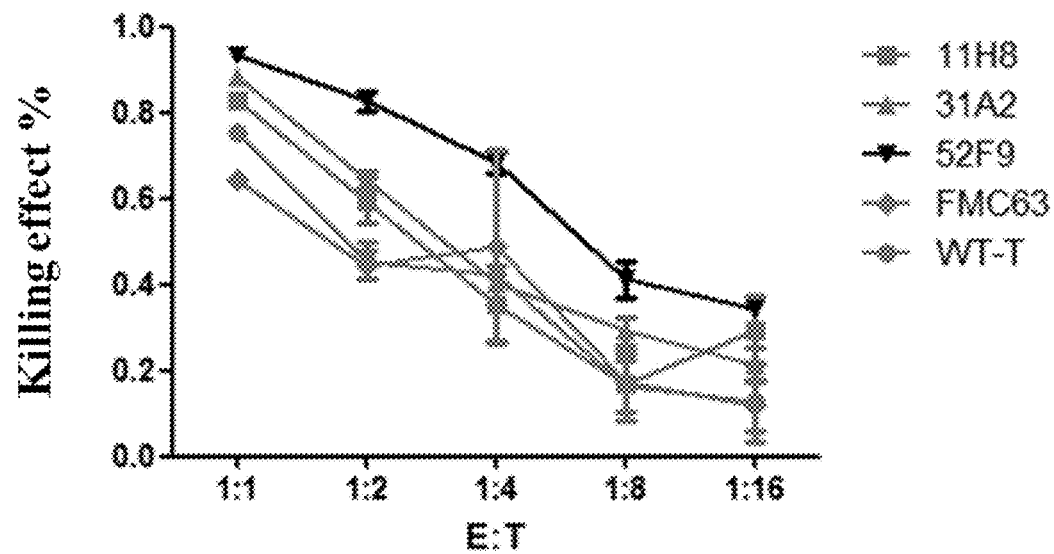
FIG. 16 shows the results of killing gastric cancer cell line MKN28 in vitro by CAR (11H8/31A2/52F9/FMC63)-41BB-TLR2-CD3ζ T cells.
Figure 17:
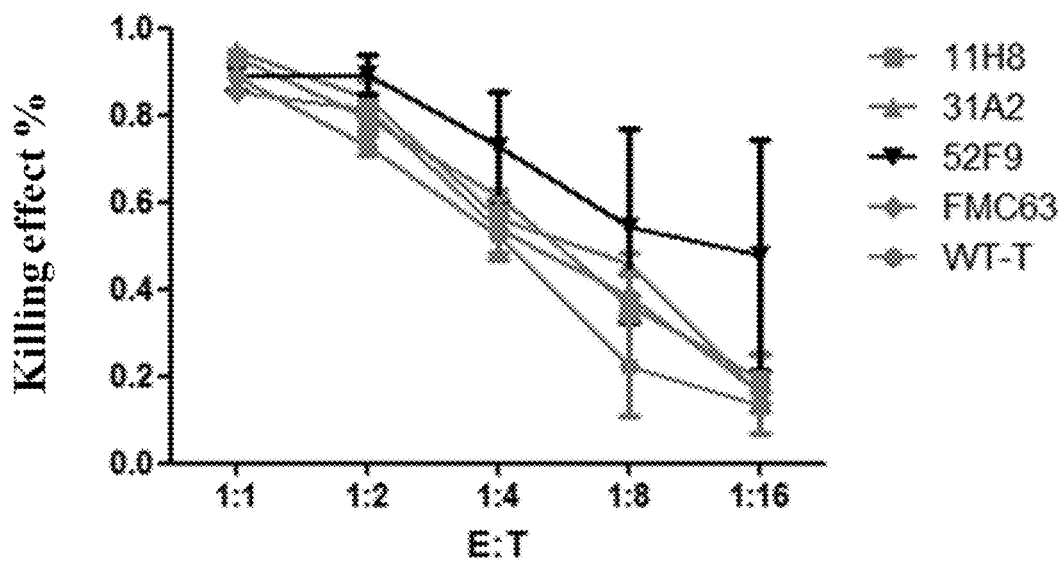
FIG. 17 shows the results of killing gastric cancer cell line SNU-1 in vitro by CAR (11H8/31A2/52F9/FMC63)-CD28-TLR2-CD3ζ T cells.
Figure 18:
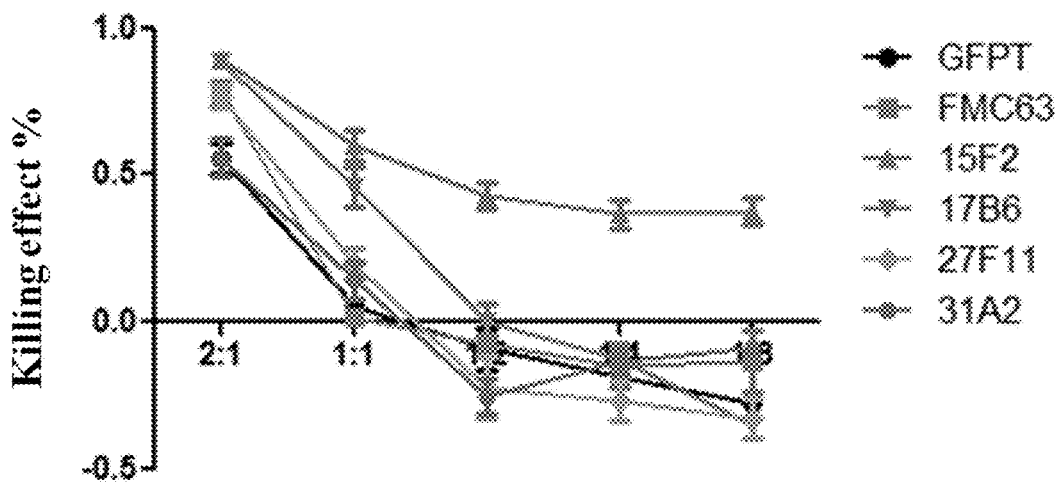
FIG. 18 shows the results of killing gastric cancer cell line SNU-1 in vitro by CAR (15F2/17B6/27F11/31A2/FMC63)-41BB-DAP10×3-CD3ζ T cells.
Figure 19:
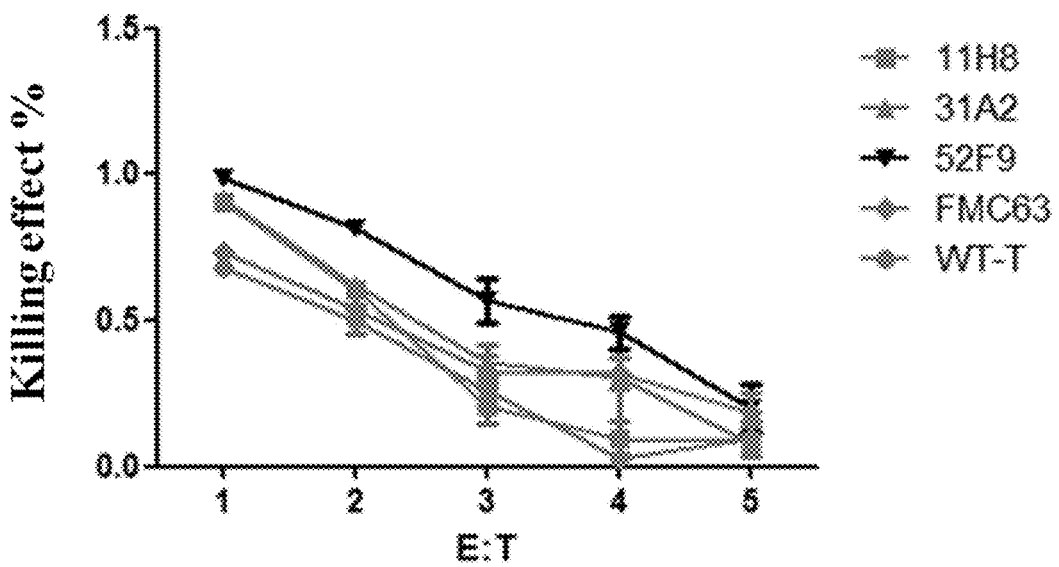
FIG. 19 shows the results of killing liver cancer cell line SMMC in vitro by CAR (11H8/31A2/52F9/FMC63)-41BB-DAP10×3-CD3ζ T cells.
Figure 20:
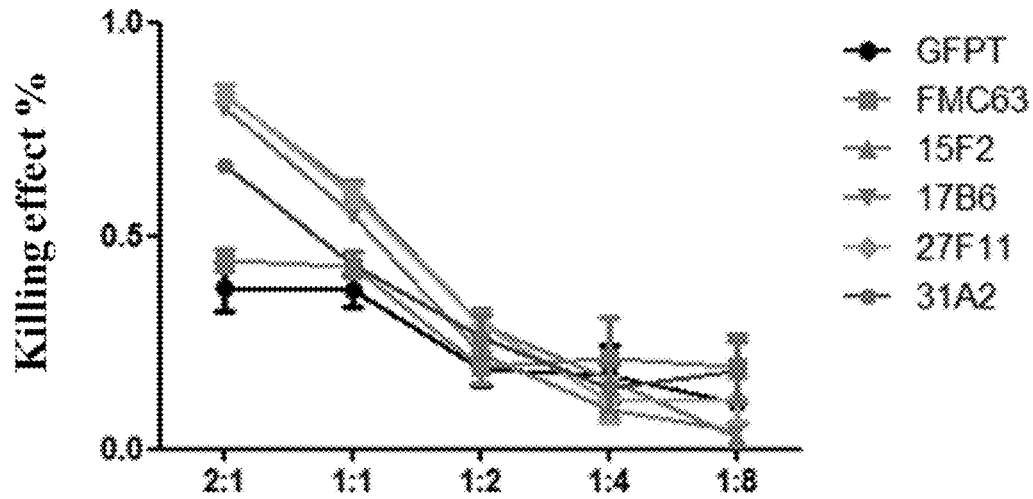
FIG. 20 shows the results of killing liver cancer cell line HepG2 in vitro by CAR (15F2/17B6/27F11/31A2/FMC63)-41BB-DAP10×3-CD3ζ T cells.

Example 12: Construction of Chimeric Antigen Receptor T Cells with the Fully Humanized CD19 Antibody Sequences (I) Construction of Chimeric Antigen Receptor Molecular Vectors pUC57-CAR 19SCFV including an anti-CD19 fully humanized monoclonal antibody SCFV sequence (the antibody sequence as shown in Table 1) was obtained by means of gene synthesis, molecular cloning, etc. (wherein the control group was FMC63). The molecular structures of CAR are shown in FIG. 7.

The obtained pUC57-CAR 19SCFV plasmids were cleaved by endonucleases PmeI and SpeI to obtain CAR 19SCFV genes, and the CAR 19SCFV genes were then connected to lentiviral vector pWPXLd (containing GFP gene) to construct pWPXLd-CAR 19S CFV-GFP.

(II) Transfection of Chimeric Antigen Receptor T Cells

The gene encoding a chimeric antigen receptor molecule can be integrated or transfected into immune cells by viral vector transduction, electroporation based on transposon system, and liposome-mediated plasmid transfection. These immune systems are then driven by a vector promoter to express the gene, so that the CAR molecular receptor is expressed on the surface of immune cells. A method of transducing T cells with lentivirus was used herein, as follows:

(1) 293T cells in logarithmic growth phase were cultured in a 150 mm Petri dish to a density of up to 80-90% (medium: DMEM high glucose medium+10% FBS (fetal bovine serum)+1% double antibody (a mixed solution of 100×penicillin-streptomycin)), and the medium was replaced with DMEM high glucose medium+1% FBS+1% double antibody. After 2-6 hours, pWPXLd-CAR-GFP or three control plasmids pWPXLd-GFP, pMD2.G and psPAX2 were co-transformed into 293T cells with PEI. At 24, 48 and 72 h after transformation, the supernatant of the medium was collected, and fresh medium (DMEM high glucose medium+1% FBS+1% double antibody) was added. The collected supernatant of the culture medium was filtered with a 0.45 uM PVDF filter to remove cell debris and reserved in a refrigerator at 4° C.

(2) Isolation and purification of T cells: Mononuclear cells in blood were isolated by Ficoll density gradient method, lysed with red blood cell lysis buffer to remove red blood cells, and then screened with MACS Pan-T magnetic beads to obtain T cells. The screened T cells were diluted to a concentration of $2.5×10^6$ cells/ml with medium AIM-V with 5% FBS, penicillin 100 U/ml and streptomycin 0.1 mg/ml. T cells were stimulated by magnetic beads coated with CD2, CD3, and CD28 antibodies (Miltenyi) according to the protocol provided by Mitianyi, that is, the ratio of magnetic beads to T cells was 1:2, and the density of T cells was $5×10^6$ cells/ml/cm$^2$, and the T cells were stimulated at 37° C. in an incubator with 5% $CO_2$ for 48 h.

(3) Transfection of T cells with lentivirus: The magnetic beads in the activated T cells were removed by magnetic field. The T cells were then centrifuged at 300 g for 5 min to remove the supernatant, and resuspended in fresh medium. The CAR lentivirus vectors as well as 8 μg/ml of polybrene and 300 IU/ml of IL-2 were added, respectively, wherein the viruses were added at an amount of MOI=10. After incubating at 37° C. in an incubator with 5% $CO_2$ for 24 h, the cells were centrifuged at 300 g for 5 min to remove the supernatant, and resuspended in fresh medium containing 300 IU/ml of IL-2, and incubated at 37° C. in an incubator with 5% $CO_2$.

(4) Expansion of CAR T cells: The density of CAR T cells was maintained at about $1×10^6$ cells/ml, and half of the fluid was replaced every 2-3 days. After two weeks, the number of T cells can be expanded by 100-fold. GFP-positive cells were successfully transfected CAR T cells. The ratio of GFP-positive cells was detected by flow cytometry to obtain the ratio of CAR T cells or control T cells.

Example 13: Test of Specific Killing of Tumor Cells by Fully Humanized Antibody CAR T Cells In Vitro (1) The anti-CD19 fully humanized CAR T cells (with different SCFV sequences 15F2, 17B6, 27F11, 31A2, 11H8, 31A2, 52F9) and FMC63 (murine-derived) CAR T cells prepared in Example 12 and wild-type T cells were mixed with $1×10^4$ tumor cells at different ratios. The mixture was added to a 96-well U-shaped plate. 3 replicate wells were set for each group, and a group where tumor cells alone were added was set as a positive control. After centrifugation at 250 g for 5 min, all groups were co-cultured at 37° C. in an incubator with 5% $CO_2$ for 18 h.

(2) Luciferase quantitative killing efficiency test: The tumor cells were cultured alone or co-cultured with CART cells for 18 hours, and then 100 μl/well of luciferase substrate (1×) was added to the 96-well cell culture plate. The cells were resuspended and well mixed, then immediately measured with a multifunctional microplate reader for RLU (relative light unit), with the measurement time set at 1 second. Calculation formula for killing ratio: 100%× (reading of control well−reading of test well)/reading of control well (the reading of the blank group without cells can be ignored).

When comparing the functions of recognizing and killing tumor cells expressing CD19 antigen by anti-CD19 fully humanized CAR T cells (with different SCFV sequences), FMC63 CAR T cells and wild-type T cells in vitro, the tumor cells were selected from RAJI-GL cell line and NALM6-GL (Luciferase gene). The results are shown in FIGS. 8-11. The results show that, compared with GFP-T wild-type T cells, CAR-T cells expressing 11H8, 15F2, 17B6, 27F11 or 31A2 ScFv have a stronger ability to recognize and kill CD19-positive target cells in vitro, and the killing level is essentially not lower than that of murine-derived FMC63 ScFv CAR-T cells.

When comparing the functions of recognizing and killing tumor cells not expressing CD19 antigen by anti-CD19 fully humanized CAR T cells (with different SCFV sequences), FMC63 CAR T cells and wild-type T cells in vitro (safety test of CAR T cells), the tumor cells were selected from acute myeloid leukemia cell line AML3, lung cancer cell lines A549-GL and H460-GL, gastric cancer cell lines MKN28 and SNU1, and liver cancer cell lines SMMC and HepG2 that do not express CD19 antigen. The results are shown in FIGS. 12-20. The results show that, compared with GFP-T wild-type T cells, CAR-T cells expressing anti-CD19 fully humanized ScFv have essentially no specific recognizing and killing effect on the tested CD19-negative target cells.

In summary, the CD19 antigen-recognizing and binding domain of the present disclosure has been humanized, which may reduce the occurrence of xenoimmune rejection without affecting the ability to recognize target antigens on tumor cells, thereby resulting in an improved duration of CAR-T cells in the human body, an enhanced immune ability to monitor tumor cells, a reduced tumor recurrence rate, and a corresponding extended complete remission period in patients.

The applicant declares that the products, uses and applications of the present disclosure are illustrated through the above-mentioned examples, but it is not intended that the present disclosure is limited thereto, which means that the present disclosure does not have to rely on the above detailed uses and usage modes to implement. It will be understood by those skilled in the art that various improvements to the present disclosure, substitutions of equivalents for materials of the products of the present disclosure, addition of auxiliary components and choice of specific means may be made without departing from the scope of protection and disclosure of the present disclosure.

The invention claimed is:

1. A scFv amino acid sequence capable of recognizing CD19 antigen, comprising:
   a heavy chain variable region having the sequence as shown in SEQ ID NO: 1; and a light chain variable region having the sequence as shown in SEQ ID NO: 7; or
   a heavy chain variable region having the sequence as shown in SEQ ID NO: 2; and a light chain variable region having the sequence as shown in SEQ ID NO: 8; or
   a heavy chain variable region having the sequence as shown in SEQ ID NO: 3; and a light chain variable region having the sequence as shown in SEQ ID NO: 9; or
   a heavy chain variable region having the sequence as shown in SEQ ID NO: 4; and a light chain variable region having the sequence as shown in SEQ ID NO: 10; or
   a heavy chain variable region having the sequence as shown in SEQ ID NO: 5; and a light chain variable region having the sequence as shown in SEQ ID NO: 11; or
   a heavy chain variable region having the sequence as shown in SEQ ID NO: 6; and a light chain variable region having the sequence as shown in SEQ ID NO: 12.

2. A nucleotide sequence encoding the scFv amino acid sequence according to claim 1.

3. A chimeric antigen receptor comprising at least one extracellular domain, a transmembrane domain, and at least one intracellular costimulatory signaling domain, wherein the at least one extracellular domain comprises the scFv amino acid sequence capable of recognizing CD19 antigen according to claim 1.

4. The chimeric antigen receptor according to claim 3, wherein the extracellular domain of the chimeric antigen receptor further includes a signal peptide domain.

5. The chimeric antigen receptor according to claim 4, wherein the signal peptide domain is any one of a GM-CSF signal peptide, an IL-2 signal peptide, or a CD8α signal peptide.

6. The chimeric antigen receptor according to claim 3, wherein the chimeric antigen receptor further includes a CD3 signaling domain.

7. The chimeric antigen receptor according to claim 3, wherein the intracellular costimulatory signaling domain comprises any one or a combination of at least two of human CD28 intracellular region, human 4-1BB intracellular region, human TLR1 intracellular region, human TLR2 intracellular region, human TLR3 intracellular region, human TLR4 intracellular region, human TLR5 intracellular region, human TLR6 intracellular region, human TLR7 intracellular region, human TLR8 intracellular region, human TLR9 intracellular region, human TLR10 intracellular region, human DAP10 intracellular region, human CD27 intracellular region, human OX40 intracellular region, human CD30 intracellular region, human CD40 intracellular region, human PD-1 intracellular region, human CTLA-4 intracellular region, human TIM3 intracellular region, human LAG3 intracellular region, human TGFβ intracellular region, human ICOS intracellular region, human lymphocyte function associated antigen 1 intracellular region, human CD2 intracellular region, human CD7 intracellular region, human LIGHT intracellular region, human NKG2C intracellular region, human NKG2D intracellular region, human NKp46 intracellular region, human NKp30 intracellular region, human NKp44 intracellular region, human DNAM1 intracellular region, human B7-H3 intracellular region or human CD83 intracellular region.

8. The chimeric antigen receptor according to claim 7, wherein the intracellular costimulatory signaling domain comprises any one or a combination of at least two of human CD28 intracellular region, human 4-1BB intracellular region, human TLR2 intracellular region, human DAP10 intracellular region×3, human DAP10 intracellular region×6, or human DAP10 intracellular region×9.

9. The chimeric antigen receptor according to claim 3, wherein the transmembrane domain is any one or a combination of at least two of CD3, CD8, CD28, OX40 or ICOS.

10. The chimeric antigen receptor according to claim 9, wherein the transmembrane domain is CD28.

11. A chimeric antigen receptor-expressing cell into which a nucleic acid encoding a chimeric antigen receptor according to claim 3 is introduced.

12. The chimeric antigen receptor-expressing cell according to claim 11, wherein the cell is T cell or a cell population containing T cells.

13. A pharmaceutical composition for treating a tumor, comprising the chimeric antigen receptor according to claim 3.

14. The pharmaceutical composition according to claim 13, wherein the pharmaceutical composition further comprises an immunotherapy drug and/or a small molecule drug.

* * * * *